(12) United States Patent
Ouellette et al.

(10) Patent No.: US 6,231,948 B1
(45) Date of Patent: *May 15, 2001

(54) FLUID TRANSPORT WEBS EXHIBITING SURFACE ENERGY GRADIENTS

(75) Inventors: William R. Ouellette, Cincinnati; Yann-Per Lee, Fairfield; A. Renee Haney, Cincinnati, all of OH (US); Frederick M. Langdon, Motoyama Kobe (JP); John B. Burchnall, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 08/832,715

(22) Filed: Apr. 11, 1997

Related U.S. Application Data

(63) Continuation of application No. 08/442,935, filed on May 31, 1995, now abandoned, which is a continuation-in-part of application No. 08/326,571, filed on Oct. 20, 1994, now abandoned, which is a continuation-in-part of application No. 08/268,404, filed on Jun. 30, 1994, now abandoned.

(51) Int. Cl.[7] ....................................................... B32B 3/10
(52) U.S. Cl. ............................ 428/131; 428/137; 428/138; 428/195
(58) Field of Search ................................... 428/131, 137, 428/138, 141, 143, 195, 316.6, 309.9

(56) References Cited

FOREIGN PATENT DOCUMENTS 0 255 209 A2    2/1988   (EP) .

Primary Examiner—Elizabeth M. Cole
(74) Attorney, Agent, or Firm—Edward J. Milbrada; Kevin C. Johnson; William Scott Andes

(57) ABSTRACT

The present invention pertains, in a preferred embodiment, to a fluid-pervious web comprising a first or wearer-contacting surface and a second or garment-facing surface. The web is particularly well suited for use as a topsheet on a disposable absorbent article. The first and second surfaces are separated from one another by an intermediate portion. The first surface of the web provides a structure which exhibits a surface energy less than the surface energy of the intermediate portion. In a preferred embodiment, the web exhibits a plurality of regions of comparatively low surface energy which define surface energy gradients where they interface with higher surface energy web surfaces. More particularly, the present invention pertains to a fluid-pervious web having a plurality of small-scale surface energy gradients which are oriented and located so as to effectively transport fluid away from the first or wearer-contacting surface. The web essentially retains its visual, tactile, and physical properties of the substrate material while achieving the desired surface energy properties. Fluid transport webs according to the present invention preferably include discontinuous, spaced regions defining small scale surface energy gradients on the first surface to aid in small scale fluid movement toward apertures or capillary entrances for transport away from the first surface. Such webs also preferably include small scale surface energy gradients normal to the first surface within a capillary structure to aid in moving fluid away from the first surface and into the capillaries for capillary fluid transport. Web materials suitable for use in the present invention include apertured formed films, apertured and non-apertured nonwoven materials, composite structures, and the like.

31 Claims, 9 Drawing Sheets

FLUID TRANSPORT WEBS EXHIBITING SURFACE ENERGY GRADIENTS

CROSS-REFERENCE TO RELATED APPLICATION

This is a continuation of application Ser. No. 08/442,935, filed on May 31, 1995, now abandoned.

This application is a continuation of application Ser. No. 08/442,935, now abandoned, which is a continuation-in-part of application Ser. No. 08/326,571, filed Oct. 20, 1994, now abandoned which is a continuation-in-part of application Ser. No. 08/268,404, filed Jun. 30, 1994, now abandoned.

FIELD OF THE INVENTION

The present invention relates to a web which is suitable for use as a fluid transport mechanism. In particular, the web is designed to facilitate fluid transport in a preferential direction from one surface toward another surface and resist fluid transport in the opposite direction.

BACKGROUND OF THE INVENTION

It has long been known in the field of disposable absorbent articles that it is extremely desirable to construct absorptive devices, such as disposable diapers, sanitary napkins, incontinent briefs, bandages, wound dressings, and the like, presenting a dry surface feel to the user to improve wearing comfort and to minimize the potential for development of undesirable skin conditions due to the prolonged exposure to moisture absorbed within the article. Accordingly, it is generally desirable to promote rapid fluid transfer in a direction away from the wearer and into a retentive structure, while resisting fluid transfer in the reverse direction.

One viable prior art solution to the aforementioned problem has been to utilize a covering or topsheet on the exposed, wearer-contacting surface which comprises a web of formed, apertured thermoplastic film. Conuonly assigned U.S. Pat. No. 4,342,314, issued to Radel et al. on Aug. 3, 1982, the disclosure of which is hereby incorporated herein by reference, discloses a representative formed film of this variety. Such webs utilize capillary fluid transport to conduct fluid away from one surface (wearer-contacting) into and through the web via three-dimensional capillaries formed into the material, and then into the underlying absorbent structure. In order to address consumer concerns with regard to plastic-like appearance and feel, webs of this variety have been developed which include an interconnected structure of fiber-like appearance in the interest of generating a more cloth-like, aesthetically-pleasing appearance. In addition, apertured, formed thermoplastic film webs have been developed which further include microscopic surface texturing (microtexture) and/or microscopic apertures (microapertures) to further enhance the visual and tactile impression of such webs. Representative film webs of this variety are discloses in commonly assigned U.S. Pat. No. 4,463,045, issued to Ahr et al. on Jul. 31, 1984, and U.S. Pat. No. 4,629,643, issued Dec. 16, 1986 to Curro et al., the disclosures of which are hereby incorporated herein by reference.

Another viable prior art solution has been to utilize a fibrous material as a covering or topsheet on such articles, alone or as an overlay or laminate over other materials. A representative topsheet structure of this variety is disclosed in commonly assigned Published PCT Application WO 93/09741, published May 27, 1993 naming Aziz et al. as inventors, the disclosure of which is hereby incorporated herein by reference. Such fibrous materials may take the form of a woven or nonwoven web of a suitable fiber variety, and may or may not include discretely formed apertures in addition to the inherent porosity of the web itself. Webs of this variety also exhibit capillary fluid transport characteristics via the three-dimensional capillaries formed by interfiber spaces, likewise conducting fluid away from the wearer-contacting surface and into the underlying absorbent structure. Such webs exhibit an aesthetically-pleasing, cloth-like surface appearance and tactile impression due to the fibrous nature of the surface.

While capillary webs of the foregoing vareies are effective in transporting fluid, their effectiveness is limited in that such capillary structures can only move fluid once it reaches the capillary interior. Fluid which wets and remains on wearer contacting surfaces contributes to a "wet" tactile feeling or impression, and to the extent that such fluid may be colored or opaque also contributes to a "stained" visual impression. Surface textures naturally occurring in the material of the web or imparted thereto in formation further increase the likelihood that residual fluid will be trapped or retained on the wearer-contacting surface rather than entering capillary structures for transport away from the surface. Thus, surface topographies which contribute to desirable visual and tactile impressions when dry can also tend to retain residual fluid on the exposed surface and thus reduced desirability under in-use conditions.

Accordingly, it would be desirable to provide a web with enhanced effectiveness in transporting fluid away from one surface which is initially contacted by a fluid.

More particularly, it would be desirable to retain visual and tactile properties of webs having fibrous or otherwise textured surfaces while promoting more rapid and more complete fluid transport away from the wearer-contacting surface and into the interior of an associated absorbent article.

SUMMARY OF THE INVENTION

The present invention pertains, in a preferred embodiment, to a fluid-pervious web comprising a first or wearer-contacting surface and a second or garment-facing surface. The web is particularly well suited for use as a topsheet on a disposable absorbent article. The first and second surfaces are separated from one another by an intermediate portion. The first surface of the web provides a structure which exhibits a surface energy less than the surface energy of the intermediate portion. In a preferred embodiment the web exhibits a plurality of regions of comparatively low surface energy which define surface energy gradients where they interface with higher surface energy web surfaces.

More particularly, the present invention pertains to a fluid-pervious web having a plurality of small-scale surface energy gradients which are oriented and located so as to effectively transport fluid away from the first or wearer-contacting surface. The web essentially retains its visual, tactile, and physical properties of the substrate material while achieving the desired surface energy properties.

Fluid transport webs according to the present invention preferably include discontinuous, spaced regions defining small scale surface energy gradients on the first surface to aid in small scale fluid movement toward apertures or capillary entrances for transport away from the first surface. Such webs also preferably include small scale surface energy gradients normal to the first surface within a capillary structure to aid in moving fluid away from the first surface and into the capillaries for capillary fluid transport.

The present invention also pertains to absorbent articles which preferably include a topsheet, a backsheet secured to the topsheet, and an absorbent core positioned between the topsheet and the backsheet, wherein the topsheet exhibits surface energy gradients according to the present invention.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE PRESENT INVENTION

Figure 1:
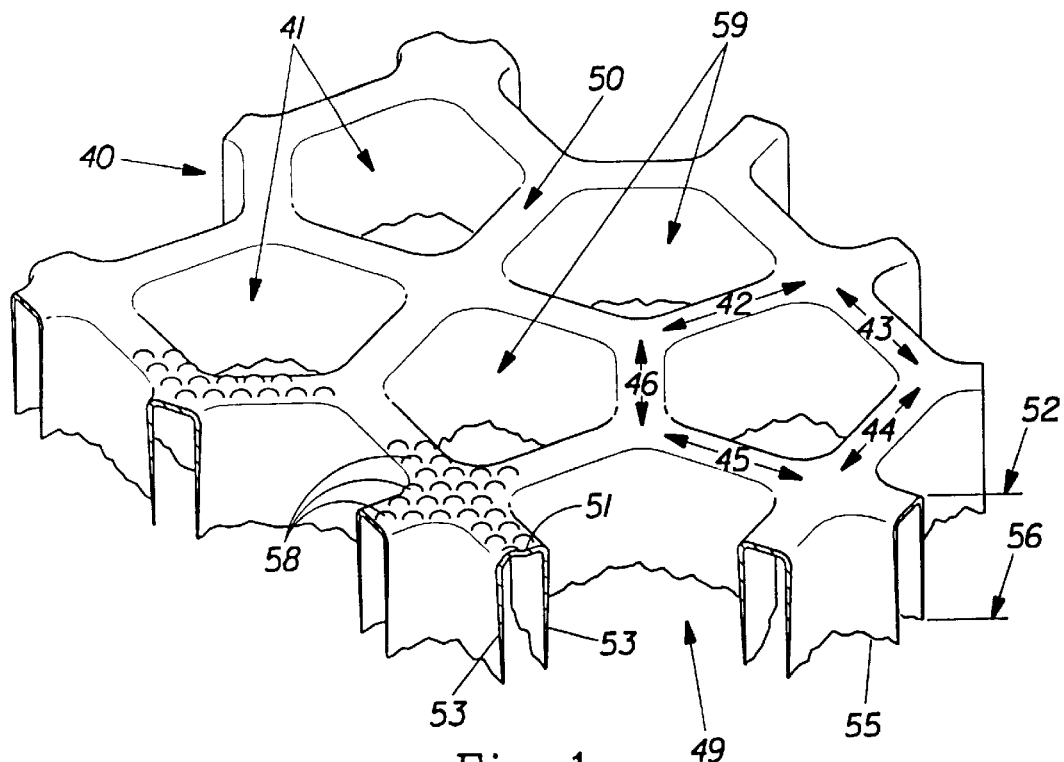
FIG. 1 is an enlarged, partially segmented, perspective illustration of a prior art plastic web of the type generally disclosed in U.S. Pat. No. 4,342,314.
Figure 14:
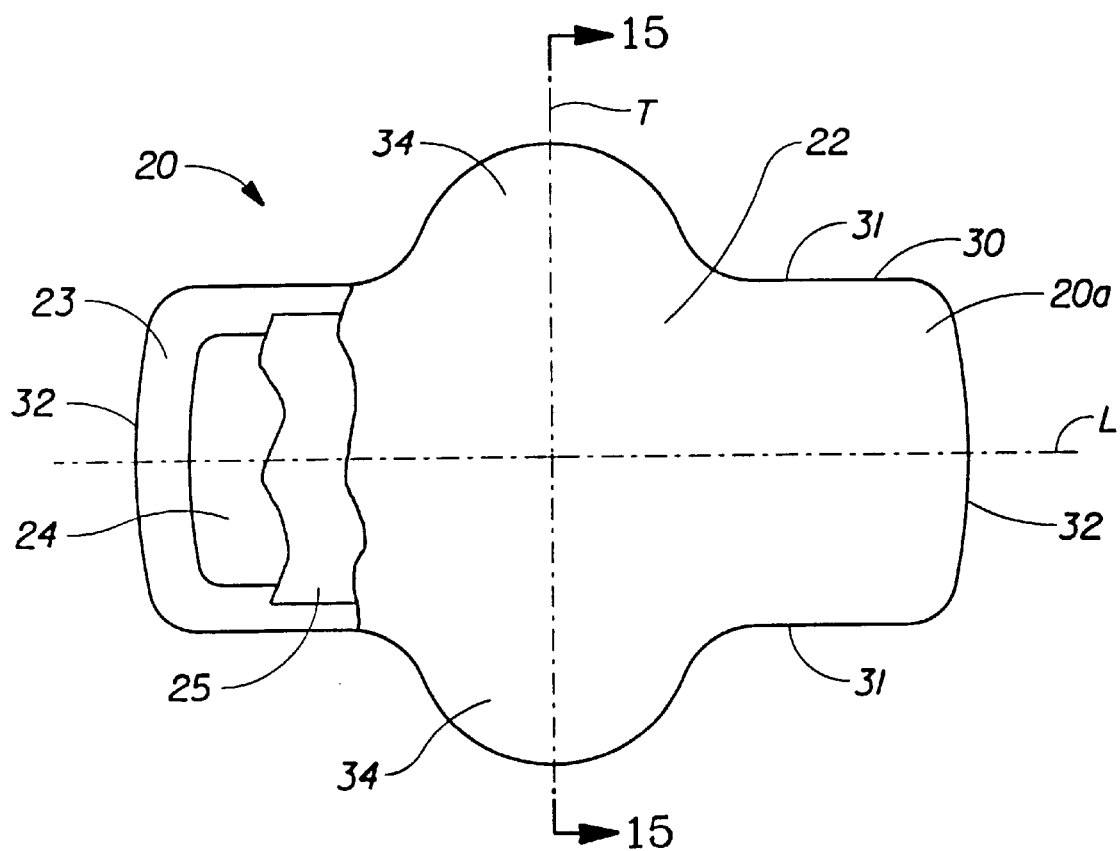
FIG. 14 is a top plan view of a sanitary napkin with portions of the sanitary napkin cut away to more clearly show the construction of the sanitary napkin.
Figure 15:
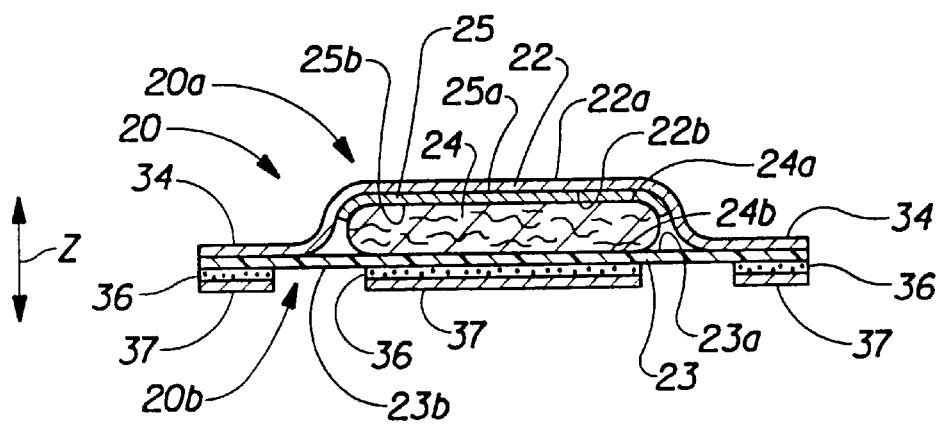
FIG. 15 is a cross-sectional view of the sanitary napkin of FIG. 14 taken along section line 15—15.

FIG. 1 is an enlarged partially segmented, perspective illustration of a prior art resilient, three-dimensional, fluid pervious plastic web 40 exhibiting a combination of fiber-like and plastic properties which has been found highly suitable for use as a topsheet in disposable absorbent articles, such as a sanitary napkin topsheet 22 in a sanitary napkin 20 of the type generally illustrated in FIGS. 14 and 15. The prior art web 40 is generally in accordance with the teachings of commonly assigned U.S. Pat. No. 4,342,314 issued to Radel et al. on Aug. 3, 1982, the disclosure of which is hereby incorporated herein by reference. The fluid pervious plastic web 40 exhibits a multiplicity of apertures (e.g., apertures 41) which are formed by a multiplicity of intersecting fiber-like elements (e.g., elements 42, 43, 44, 45, and 46) interconnected to one another in the first or wearer-contacting surface 50 of the web. Each fiber-like element comprises a base portion (e.g., base portion 51) located in plane 52, and each base portion has a sidewall portion (e.g., sidewall portions 53) attached to each edge thereof. The sidewall portions preferably extend generally in the direction of the second surface 55 of the web, with the intersecting sidewall portions of the fiber-like elements interconnected to one another intermediate the first and second surfaces of the web, terminating substantially concurrently with one another in the plane 56 of the second surface 55.

The term "fiber-like", as utilized herein to describe the appearance of plastic webs, refers generally to any fine scale pattern of embossments or apertures, random or non-random, reticulated or non-reticulated, which can provide an overall appearance and impression of a woven or nonwoven fibrous web when viewed by the human eye. When describing the elements used to form the web, the term "fiber-like" is utilized herein to describe the appearance or shape of the elements. As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to a normal human eye when the perpendicular distance between the viewers eye and the plane of the web is about 12 inches.

In general, as utilized herein the term "macroscopic" is used to refer to structural features or elements which are readily visible to a normal human eye when the perpendicular distance between the viewers eye and the plane of the web is about 12 inches. Conversely, the term "microscopic" is utilized to refer to structural features or elements which are not readily visible to a normal human eye when the perpendicular is distance between the viewer's eye and tee plane of the web is about 12 inches.

Such macroscopically expanded webs, ribbons and films are typically caused to conform to the surface of said forming structures by embossing (i.e., when the forming structure exhibits a pattern comprised primarily of male projections), by debossing (i.e., when the forming structure exhibits a pattern comprised primarily of female capillary networks), or by extrusion of a resinous melt onto the surface of a forming structure of either type. By way of contrast, the term "planar" when utilized herein to describe plastic webs, ribbons and films, refers to the overall general condition of the web, ribbon and film when viewed by the naked eye on a macroscopic scale.

In a particularly preferred embodiment, the interconnected sidewall portions 53 terminate substantially concurrently with one another in the plane 56 of the second surface 55 to form apertures 49 in the second surface 55 of the web. The capillary networks 59 formed by the interconnected sidewall portions allows for the free transfer of fluid from the first or wearer-contacting space 50 of the web directly to the second surface 55 of the web without lateral transmission of fluid between adjacent capillary networks.

Each of the fiber-like elements exhibits a substantially uniform U-shaped cross-section along its length. In the case of a primary fiber-like element, its cross-section comprises a base portion located in the wearer-contacting plane and a sidewall portion joined to each edge of the base portion and extending generally in the direction of the absorbent pad-contacting surface of the web. The sidewad portions which intersect one another are joined to one another intermediate the wearer-contacting surface and the absorbent pad-contacting surface of the web, thereby forming a capillary network interconnecting the opposed surfaces of the web.

One drawback associated with the use of topsheets comprised of plastic is that despite their superior fluid handling characteristics some users are very reluctant to place a topsheet which they readily perceive as plastic by virtue of its glossy appearance in contact with their skin. To reduce the gloss on the web's visible surface, i.e., that portion of the web which is visible from directly overhead, it has been learned that the inclusion of a microscopic pattern of surface aberrations which are not discernible when the perpendicular distance between the viewer's eye and the plane of the web is about 12 inches is highly effective. Conmnonly assigned U.S. Pat. No. 4,463,045, issued to Ahr et al. on Jul. 31, 1984, the disclosure of which is hereby incorporated herein by reference, defines the relevant criteria which must be satisfied so that the three-dimensionally expanded web will exhibit a substantially non-glossy visible surface.

In a particularly preferred embodiment, the base portion 51, includes a microscopic pattern of surface aberrations 58, generally in accordance with the teachings of the aforementioned '045 Ahr et al. patent. The microscopic pattern of surface aberrations 58 provides a substantid non-glossy visible surface when the web is struck by incident light rays.

A topsheet of the type generally disclosed in Radel et al., having surface aberrations according to Ahr et al., exhibits a fiber-like appearance and tactile impression as well as a non-glossy visible surface. In addition, it is highly effective in promoting rapid fluid transfer from the first or wearer-contacting surface to the second or absorbent pad-contacting surface of the topsheet. Topsheets of the latter type have enjoyed widespread commercial success on catamenial pads due to their clean and dry appearance in use when contrasted to conventional nonwoven fibrous topsheets.

Typically, a prior art web 40 used as a topsheet on an absorbent article is treated with a surfactant to render the topsheet hydrophilic. The exposed surfaces of the base portions 51 and the sidewall portions 53 are generally treated with a surfactant such that they will both be rendered substantially hydrophilic, thereby diminishing the likelihood that body fluids will flow off the topsheet rather than being drawn through the topsheet and thereby absorbed by the absorbent core. Suitable methods of applying surfactants are described in U.S. Pat. Nos. 4,950,254 and 5,009,563, both issued to Thomas Osborn, the disclosures of which are hereby incorporated herein by reference.

Despite the effective functioning of the surfactant treated prior art fluid-pervious web 40 in topsheet applications for disposable absorbent articles such as sanitary napkins there can be perceived drawbacks associated with topsheets of similar construction. For example, treating the entire exposed surface of the topsheet with a surfactant creates a very wettable surface which, when placed into contact with the wearer's skin, may cause the topsheet to stick to the wearers skin. This in turn may create a hot, sweaty, and/or sticky sensation for the user which may be viewed as less desirable by some users.

In addition, although capillary web structures of the foregoing varieties are effective in transporting fluid, their effectiveness is limited in that such capillary structures can only move fluid once it reaches the interior of the capillaries. Fluid which wets and remains on wearer contacting surfaces contributes to a "wet" tactile feeling or impression, and to the extent that such fluid may be colored or opaque also contributes to a "stained" visual impression. Surface textures naturally occurring in the material of the web or imparted thereto in formation further increase the likelihood that residual fluid will be trapped or retained on the wearer-contacting surface rather than entering capillary structures for transport away from the surface. Thus, surface topographies which contribute to desirable visual and tactile impressions when dry can also tend to retain residual fluid on the exposed surface and thus reduced desirability under in-use conditions.

Figure 2:
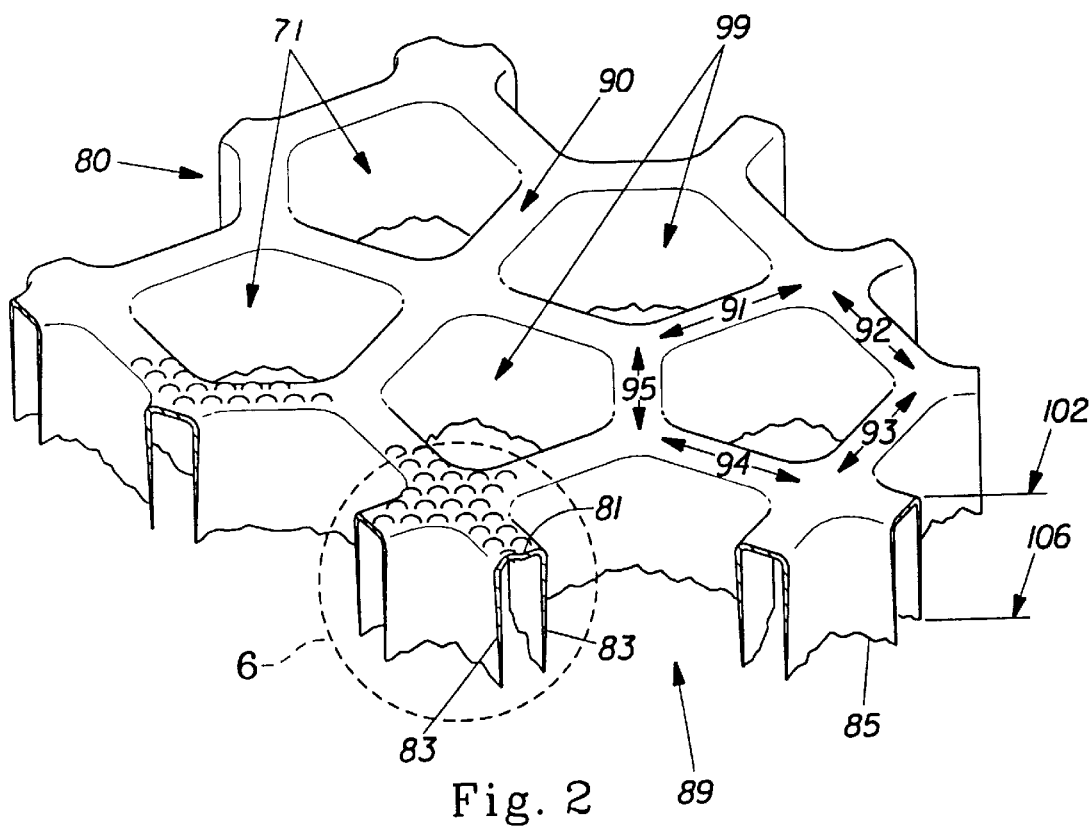
FIG. 2 is an enlarged, partially segmented perspective illustration of a preferred plastic web of the present invention having a surface energy gradient.

FIG. 2 is an enlarged partally segmented, perspective illustration of a three-dimensional, fiber-like, fluid-pervious formed-film web embodiment of the present invention, generally indicated as 80. The geometrical configuration of the fluid pervious web 80 is generally similar to that of prior art web 40 illustrated in FIG. 1 and is generally in accordance with the teachings of the aforementioned '314 Radel et al. patent. Other suitable formed films are described in U.S. Pat. No. 3,929,135, issued to Thompson on Dec. 30, 1975; U.S. Pat. No. 4,324,246 issued to Mullane, et al. on Apr. 13, 1982; and U.S. Pat. No. 5,006,394 issued to Baird on Apr. 9, 1991. The disclosures of each of these patents are hereby incorporated herein by reference. The web 80 is preferably made from a thermoplastic film. Examples of suitable materials for use as the web 80 include but are not limited to polyolefins such as polyethylenes, including linear low density polyethylene, low density polyethylene, ultra low density polyethylene, high density polyethylene, and polypropylene; metallocene catalyst-based polymers; nylon (polymide); cellulose esters; poly (methyl methacrylate); polystyrene; poly (vinyl chloride); polyester, polyurethane; compatible polymers; compatible co-polymers; biodegradable polymers; and blends, laminates and/or combinations thereof. Films made from such materials may be plasticized with suitable additives known in the art Other additives may be added to achieve the desired physical characteristics.

The fluid pervious plastic web 80 exhibits a multiplicity of apertures or fluid passageways (e.g., apertures 71) which are formed by a multiplicity of intersecting fiber-like elements (e.g., elements 91, 92, 93, 94, and 95) interconnected to one another in the first or wearer-contacting surface 90 of the web. Each fiber-like element comprises a base portion (e.g., base portion 81) located in plane 102, and each base portion has a sidewall portion (e.g., sidewall portions 83) attached to each edge thereof. The sidewall or intermediate portions 83 extend generally in the direction of the second surface 85 of the web. The intersecting sidewall portions of the fiber-like elements are interconnected to one another intermediate the first and second surfaces of the web, and terminate substantially concurrently with one another in the plane 106 of the second surface 85.

As utilized herein, the term "fluid passageway" is intended to encompass enclosed or at least partially enclosed structures or channels which may communicate fluids. The term fluid passageway is thus intended to encompass the terms "aperture", "channel", "capillary", as well as other similar terms.

In a particularly preferred embodiment, the interconnected sidewall or intermediate portions 83 teminate substantially concurrently with one another in the plane 106 of the second surface 85 to form apertures 89 in the second surface 85 of the web. The capillary networks 99 formed by the interconnected sidewall or intermediate portions 83 allow for the free transfer of fluid from the first or wearer-contacting surface 90 of the web directly to the second surface 85 of the web without lateral transmission of fluid between adjacent capillary networks.

Figure 3:
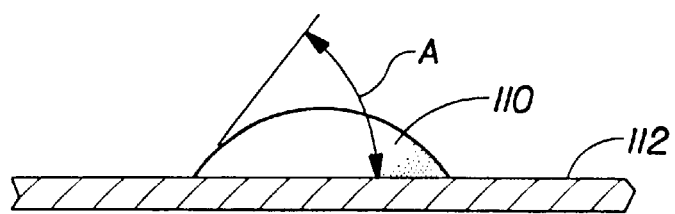
FIG. 3 is an enlarged cross-sectional view of a droplet of liquid on a solid surface, where angle A illustrates the contact angle of the liquid with the solid surface.

In accordance with the present invention, the first or wearer-contacting surface 90 of web 80 is relatively non-wettable compared to the relatively wettable intermediate or sidewall portions 83. A useful parameter of wettability is the contact angle that a drop of liquid (gas-liquid interface) makes with the solid surface (gas-solid interface). Typically, a drop of liquid 110 placed on a solid surface 112 makes a contact angle, A, with the solid surface, as seen in FIG. 3. As the wettability of the solid surface by the liquid increases, the contact angle, A, decreases. As the wettability of the solid surface by the liquid decreases, the contact angle, A, increases. The liquid-solid contact angle may be determined from techniques known in the art, such as those described in greater detail in *Physical Chemistry of Surfaces*, Second Edition, by Arthur W. Adamson (1967), F. E. Barteli and H. H. Zuidema, *J. Am. Chem. Soc.*, 58, 1449 (1936), and J. J. Bikerman, *Ind. Eng. Chem., Anal. Ed.*, 13, 443 (1941), each of which are hereby incorporated herein by reference. More recent publications in this area include Cheng, et al., *Colloids and Surfaces* 43:151–167 (1990), and Rotenberg, et al., *Journal of Colloid and Interface Science* 93(1):169–183 (1983), which are also hereby incorporated herein by reference.

As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. This is discussed in detail in the American Chemical Society publication entitled *Contact Angle, Wettability and Adhesion*, edited by Robert F. Gould (Copyright 1964), which is hereby incorporated herein by reference. A surface is said to be wetted by a fluid (hydrophilic) when the fluid tends to spread spontaneously across the surface. Conversely, a surface is considered to be "hydrophobic" if the fluid does not tend to spread spontaneously across the surface.

The contact angle depends on surface inhomogeneities (e.g., chemical and physical properties, such as roughness), contamination, chemical/physical treatment of or composition of the solid surface, as well as the nature of the liquid and its contamination. The surface energy of the solid also influences the contact angle. As the surface energy of the solid decreases, the contact angle increases. As the surface energy of the solid increases, the contact angle decreases.

The energy required to separate a liquid from a solid surface (e.g., a film or fiber) is expressed by equation (1):

$$W = G(1 + \cos A) \tag{1}$$

where:

W is the work of adhesion measured in $erg/cm^2$,

G is the surface tension of the liquid measured in dyne/cm, and

A is the liquid-solid contact angle measured in degrees.

With a given liquid, the work of adhesion increases with the cosine of the liquid-solid contact angle (reaching a maximum where the contact angle A is zero).

Work of adhesion is one useful tool in understanding and quantifying the surface energy characteristics of a given surface. Another useful method which could be utilized to characterize the surface energy characteristics of a given surface is the parameter labeled "critical surface tension", as discussed in H. W. Fox, E. F. Hare, and W. A. Zisman, *J. Colloid Sci.* 8, 194 (1953), and in Zisman, W. A., *Advan. Chem. Series No.* 43. Chapter 1, American Chemical Society (1964), both of which are hereby incorporated herein by reference.

Illustrated below in Table 1 is the inverse relationship between contact angle and work of adhesion for a particular fluid (e.g., water), whose surface tension is 75 dynes/cm.

TABLE 1

| A (degrees) | cos A | 1 + cos A | W ($erg/cm^2$) |
|---|---|---|---|
| 0 | 1 | 2 | 150 |
| 30 | 0.87 | 1.87 | 140 |
| 60 | 0.5 | 1.50 | 113 |
| 90 | 0 | 1.00 | 75 |
| 120 | −0.5 | 0.5 | 38 |
| 150 | −0.87 | 0.13 | 10 |
| 180 | −1 | 0 | 0 |

As depicted in Table 1, as the work of adhesion of a particular surface decreases (exhibiting a lower surface energy of the particular surface), the contact angle of the fluid on the surface increases, and hence the fluid tends to "bead up" and occupy a smaller surface area of contact. The reverse is likewise true as the surface energy of a given surface decreases with a given fluid. The work of adhesion, therefore, influences interfacial fluid phenomena on the solid surface.

Figure 4:
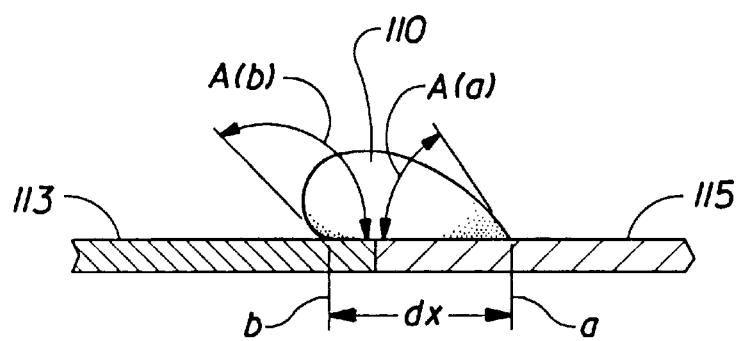
FIG. 4 is an enlarged cross-sectional view of a droplet of liquid on a solid surface having two different surface energies, thus exhibiting two different contact angles A(a) and A(b)

More importantly, in the context of the present invention, surface energy gradients or discontinuities have been found to be useful in promoting fluid transport. FIG. 4 illustrates a droplet of fluid 110 which is located on a solid surface having two regions 113 and 115 having differing surface energies (indicated by the different cross-hatching for illustrative purposes). In the situation illustrated in FIG. 4, region 113 exhibits a comparatively lower surface energy than region 115, and hence a reduced wettability for the fluid of the droplet than region 115. Accordingly, the droplet 110 produces a contact angle A(b) at the edge of the droplet contacting region 113 which is greater than the contact angle A(a) produced at the edge of the droplet contacting region 115. It should be noted that although for graphic clarity the points "a" and "b" lie in a plane, the distance "dx" between poits "a" and "b" need not be linear, instead representing the extent of droplet/surface contact regardless of the shape of the surface. Droplet 110 thus experiences a surface energy imbalance and hence an external force due to the differences in the relative surface energies (i.e., the surface energy gradient or discontinuity) between regions 113 and 115, which can be represented by the equation (2):

$$dF = G[\cos A(a) - \cos A(b)]dx \quad (2)$$

where:

dF is the net force on the fluid droplet, dx is the distance between the reference locations "a" and "b", G is as defined previously, and A(a), and A(b) are the contact angles A at locations "a" and "b", respectively.

Solving equation (1) for cos A(a) and cos A(b) and substituting into equation (2) yields equation (3):

$$dF = G[(W(a)/G-1) - (W(b)/G-1)]dx \quad (3)$$

Equation (3) can be simplified to equation (4):

$$dF = (W(a) - W(b))dx \quad (4)$$

The importance of the differential in surface energy between the two surfaces is clearly depicted in equation (4), as is the directly proportional effect that changes in the magnitude of the differential in work of adhesion would have on the magnitude of the force.

More detailed discussions of the physical nature of surface energy effects and capillarity may be found in *Textile Science and Technology*, Volume 7, *Absorbency*, edited by Portnoy K. Chatteijee (1985), and *Capillary, Theory and Practice*, Ind. Eng. Chem. 61,10 (1969) by A. M. Schwartz, which are hereby incorporated herein by reference.

Accordingly, the force experienced by a droplet will cause movement in the direction of the higher surface energy. For simplicity and graphic clarity, the surface energy gradient or discontinuity has been depicted in FIG. 4 as a single, sharp discontinuity or boundary between well-defined regions of constant but differing surface energy. Surface energy gradients may also exist as a continuous gradient or a stepwise gradient, with the force exerted on any particular droplet (or portions of such droplet) being determined by the surface energy at each particular area of droplet contact.

As used herein, the term "gradient" when applied to differences in surface energy or work of adhesion is intended to describe a change in surface energy or work of adhesion occurring over a measurable distance. The term "discontinuity" is intended to refer to a type of "gradient" or transition, wherein the change in surface energy occurs over an essentially zero distance. Accordingly, as used herein all "discontinuities" fall within the definition of "gradient".

Also, as used herein the terms "capillary" and "capillarity" are used to refer to passageways, apertures, pores, or spaces within a structure which are capable of fluid transport in accordance with the principles of capillarity generally represented by the Laplace equation (5):

$$p = 2G(\cos A)/R \quad (5)$$

where:

p is the capillary pressure;

R is the internal radius of the capillary (capillary radius); and

G and A are as defined above.

As noted in *Penetration of Fabrics* by Emery I. Valko, found in Chapter III of *Chem. Aftertreat. Text.* (1971), pp. 83–113, which is hereby incorporated herein by reference, for A=90°, the cosine of A is zero and there is no capillary pressure. For A>90°, the cosine of A is negative and the capillary pressure opposes the entry of fluid into the capillary. Hence, the capillary walls must be of a hydrophilic nature (A<90°) for capillary phenomena to occur. Also, R must be sufficiently small for p to have a meaningful value, since as R increases (larger aperture/capillary structure) the capillary pressure decreases.

Perhaps at least as important as the presence of surface energy gradients is the particular orientation or location of the gradients themselves with respect to the orientation and location of the capillaries or fluid passageways themselves. More particularly, the surface energy gradients or discontinuities are located in relation to the capillaries such that fluid cannot reside on the first or upper surface without contacting at least one surface energy gradient or discontinuity and thus experience the driving force accompanying the gradient. Fluid moved to or otherwise present at a capillary entrance will preferably contact at least one Z-direction gradient or discontinuity present in the capillary itself near the capillary entrance, and thus experience the Z-direction driving force to drive the fluid into the capillary where capillary forces take over to move the fluid away from the first surface. In a preferred configuration, the capillaries preferably exhibit a low surface energy entrance length and an otherwise higher surface energy capillary wall or surface such that the surface energy gradient or discontinuity is a comparatively small but finite distance below the first surface. In such a location the discontinuity or gradient is positioned such that fluid in contact with the first surface at the edge of the capillary or over the open end of the capillary will have a lower surface or meniscus which will extend downwardly into the open end of the capillary where it will contact the discontinuity.

Figure 5:
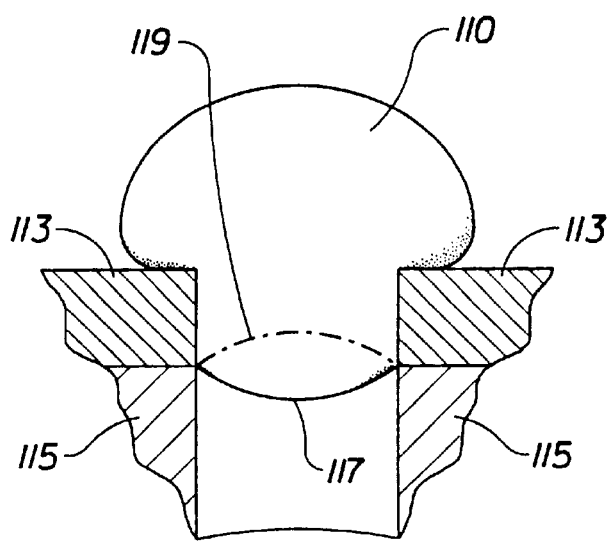
FIG. 5 is an enlarged cross-sectional view of a droplet of liquid located adjacent a generic capillary exhibiting a surface energy gradient.

By way of further explanation of this principle, FIG. 5 depicts a droplet 110 of a fluid which is located over a generic capillary or fluid passageway. This representation is intended to be sufficiently generic as to represent the concept expressed herein without being limited to a particular web material, design, or construction. Analogously to FIG. 4, the capillary is formed so as to present surfaces 113 and 115 having different surface energies (indicated by the different cross-hatching for illustrative purposes). As in FIG. 4, the surface energy of surface 113 is at a predetermined level which is comparatively low in comparison with that of surface 115, such that surface 113 is regarded as hydrophobic. Accordingly, the droplet edges in contact with surface 113 will exhibit a relatively larger contact angle A such that the droplet edges make a sharp departure from the interface with surface 113. Surface 115, on the other hand, has a comparatively higher surface energy in comparison with surface 113.

In the situation depicted in FIG. 5, the droplet 110 is located over and extends partially into the entrance of the capillary in a condition where the surface tension forces and gravitational forces are roughly in equilibrium. The lower portion of the droplet which is within the capillary forms a meniscus 117, with its edges in contact with the capillary wall in the region 113 having hydrophobic surface energy characteristics. The surface energy gradient, discontinuity, or transition between surfaces 113 and 115 is particularly determined so as to contact the lower portion of the droplet in the vicinity of the edge of the meniscus 117. The orientation of the droplet and depth of the meniscus of the droplet are determined by such factors as fluid viscosity, fluid surface tension, capillary size and shape, and the surface energy of the upper surface and capillary entrance.

At the instant when the droplet positions itself over the capillary entrance and the lower edge of the droplet contacts the Z-direction surface energy gradient, discontinuity, or transition between surfaces 113 and 115, the meniscus 117 which is of a convex shape reverts to a concave-shaped meniscus such as meniscus 119 depicted in dot-dash line form. When the meniscus changes to a concave form such as meniscus 119, the fluid wets the capillary wall in the vicinity of the upper region of the hydrophilic surface 115 and the fluid experiences an external force due to the surface energy differential described above in equation (3). The combined surface energy and capillary pressure forces thus act in concert to draw the fluid into the capillary for capillary fluid transport away from the first surface. As the fluid droplet moves downward into the capillary, the comparatively low surface energy nature of the surface 113 at the upper region of the capillary minimizes the attraction of the fluid to the upper surface and minimizes drag forces on the droplet, reducing the incidence of fluid hang-up or residue on or near the upper surface.

Water is used as a reference liquid throughout only as an example for discussion purposes, and is not meant to be limiting. The physical properties of water are well-established, and water is readily available and has generally uniform properties wherever obtained. The concepts regarding work of adhesion with respect to water can easily be applied to other fluids such as blood, menses and urine, by taking into account the particular surface tension characteristics of the desired fluid.

Referring to FIG. 2, while the first or wearer-contacting surface 90 of web 80 has a relatively low surface energy and a relatively low work of adhesion for a given fluid (e.g., water, or bodily fluids such as menses), the sidewall or intermediate portions 83 of the web 80 preferably have a relatively high surface energy and a relatively high work of adhesion for a given fluid. Since the intermediate portions 83 of the web 80 have a relatively higher surface energy as compared to the first surface 90, the intermediate portions 83 are more wettable than the first surface 90.

The second surface 85 of the web 80 preferably has a higher surface energy and a higher work of adhesion for fluid than that of the first surface 90. The surface energy and work of adhesion for fluid of second surface 85 may be the same as that of the intermediate portion 83. In a preferred embodiment, the surface energy and work of adhesion for fluid of the second surface 85 are relatively higher than that of the intermediate portion 83.

By having a web with a surface energy gradient formed by structures creating a relatively low surface energy adjacent the portion of the web which will be placed adjacent to and in contact with the wearer's skin (i.e., the first surface 90), and a relatively higher surface energy portion located away from contact with the wearers skin (i.e., the sidewall or intermediate portions 83), the web 80 will be capable of moving a drop of liquid from the portion of the web exhibiting the relatively lower surface energy to the portion of the web exhibiting the relatively higher surface energy. The motion of the drop of liquid is induced by the contact angle differential between the lower surface energy portion and the higher surface energy portion which results in an imbalance in surface tension force acting on the solid-liquid contact plane. It is believed that this resulting surface energy gradient, which enhances the fluid handling properties of the web 80 of the present invention and which makes the web well suited for use as a topsheet on an absorbent article, such as topsheet 22 on absorbent article 20 illustrated in FIG. 14.

In addition to the enhanced fluid handling properties, by designing the web so that its relatively lower surface energy portion can be placed in contact with the wearer's skin, the adhesion between the skin and the web is reduced by decreasing the capillary force generated by occlusive body fluids located between the first surface of the web and the wearer's skin. By providing a structure with reduced adhesion between the wearer's skin and the web, the sensation or impression of stickiness associated with adhesion to a plastic web topsheet is also reduced.

The potential for rewet is also reduced by having a topsheet with a surface energy gradient according to the aforementioned description. As use forces tend to force the collected fluid to rewet or be squeezed out of the pad (e.g., squeezed by compression from the absorbent core towards the first surface of the topsheet), such undesirable movement will be resisted by the first surface of the topsheet which has a relatively low surface energy to repel the fluid as it attempts to make its way out of the pad through the openings in the topsheet.

Furthermore, fluid is able to enter the topsheet more quickly due to the driving forces of the surface energy gradients of the topsheet. Fluid is moved in the "Z" direction toward the second surface of the topsheet via the surface energy gradients from the first surface energy to the relatively higher surface energy of the sidewall portions of the topsheet toward the absorbent core.

With regard to the surface energy gradients of the present invention, it is important to remember that the upper and lower bounds of any such gradient are relative with respect to one another, i.e., the regions of the web whose interface defines a surface energy gradient need not be on different sides of the hydrophobic/hydrophilic spectrum. That is to say, a gradient may be established by two surfaces of diverse degrees of hydrophobicity or diverse degrees of hydrophilicity, and need not necessarily be established with regard to a hydrophobic surface and a hydrophilic surface. Notwithstanding the foregoing, it is presently preferred that the upper surface of the web have a comparatively low surface energy, i.e., that it be generally hydrophobic, in order to maximize the driving force imparted to the incoming fluid and minimize the overall wettability of the wearer-contacting surface.

While many structures in the prior art have attempted to utilize various superficial coatings to impart greater hydrophobicity and/or reduced coefficient of friction to the overall upper surface of a web, such coatings typically substantially reduce if not eliminate topographical surface features present in the uncoated web. As discussed above, such surface features are an important physical feature with regard to visual and tactile impression. Moreover, such coatings typically have a smooth, glossy finish which accentuates the sweaty, sticky, plastic-like feel of such webs.

Without wishing to be bound by theory, surface topography is believed to play a major role in not only reducing the negative visual and tactile impressions normally associated with such webs, but also in the handling and/or transport and retention of bodily fluids. Accordingly, fluid pervious webs according to the present invention preferably are constructed so as to preserve the physical surface topography of the initially formed web, i.e., wherein the surface features survive the gradient-generating process.

Figure 6:
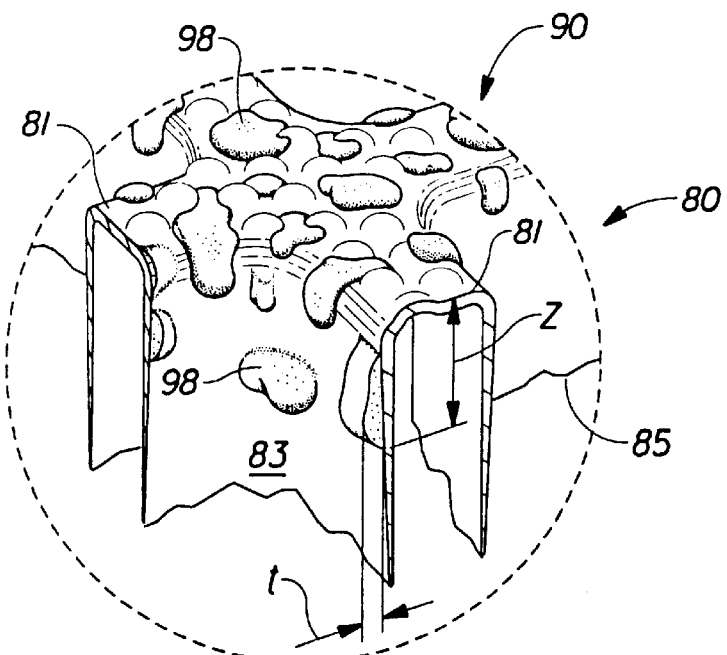
FIG. 6 is a further enlarged, partial view of the web of FIG. 2 illustrating one web construction according to the present invention.

FIG. 6 is an enlarged partial view more clearly depicting the orientation of regions 98 on the first surface 90 and in the capillaries of the formed film of FIG. 2. It should be noted that with regard to FIG. 6, as with subsequent figures, the size and shape of regions 98 have been exaggerated in resolution and thickness for graphic clarity. The randomness and irregularity of such depositions or treatments exceed the limitations of graphic depiction, and hence the illustrations herein are intended to be illustrative and not limiting. Accordingly, the regions 98 depicted in FIG. 6 are preferably also interspersed by even smaller regions which are too small and random to be depicted adequately in such an illustration. By way of reference, the surface texture in the form of microscopic aberrations (depicted at 58 in FIG. 1, not numbered but shown in FIGS. 2, 6, and 7) is (as defined by the Ahr et al. reference) at a microscopic level, and accordingly the relative size, thickness, and extent of the regions 98 can thus be appreciated.

The surface energy gradients of the present invention therefore exist in a unique relationship to the surface features and/or textures of a fluid pervious web made in accordance herewith. As depicted in greater detail in FIG. 6, the surface energy gradients are preferably constructed by forming regions 98 of low surface energy which interface with surrounding regions of the web which are of a comparatively higher surface energy. Therefore, each region 98 generates a surface energy gradient at its boundary. Accordingly, the greater the number of regions 98, the greater the number of individual surface energy gradients. Regions 98 are preferably discontinuous (i.e., not entirely encapsulating the web) and spaced, leaving intervening regions of higher surface energy.

Note also in FIG. 6 the depiction of the thickness "t" of the surface energy treatment used to generate regions 98, and the depth "Z" to which any particular region 98 extends below the first surface 90 of the web. The thickness "t" is preferably small in relation to the depth or extent "Z" of the regions 98 so as to minimize the impact of the generation of the regions on the topography of the web. In a case where the regions 98 are formed by a coating, the thickness "t" is the thickness of the coating. Where the regions are formed by altering the chemistry of the web material, the thickness "t" would be less than or at most equal to the film gauge or thickness.

At each gradient, a droplet contacting both surfaces experiences a driving force which imparts some degree of motion to the fluid and reduces the likelihood of fluid stagnation or hangup, particularly on surface topography. Although the regions 98 could be applied in a predetermined pattern, the regions 98 are preferably randomly oriented on the web surfaces, with the randomness increasing the likelihood that the surface energy gradients will be properly positioned so as to affect any particular droplet or quantity of fluid. Randomness is desirable not only across the first surface of the web, but also within the fluid passageways themselves. Accordingly, any particular capillary or passageway may exhibit multiple surface energy gradients defined by regions 98 which may also be located at differing locations in the Z-direction from the first surface. Also, particular fluid passageways may exhibit more or less regions 98 than other fluid passageways, and regions 98 may also be located so as to entirely reside within fluid passageways (i.e., be entirely located between the first and second surfaces).

The regions 98 are also preferably discontinuous in nature with respect to the surface directionality of the web. Particularly evident in FIG. 6 is that the surface treatment is preferably discontinuous with respect to the land regions of the web between successive capillaries. The discontinuity of a hydrophobic surface treatment applied to a less hydrophobic (or more hydrophllic) substrate such as the web surface results in a pattern of small-scale surface energy gradients in the plane of the surface. Such gradients are to be distinguished from large-scale X-Y gradients of a zonal nature by their smaller relative size vis-à-vis average droplet size and size of web surface details. Accordingly, as used herein the term "small-scale" is intended to refer to surface features, topography, or surface energy gradients which are smaller in magnitude than the average size of a droplet of fluid on the surface in question Average droplet size is a readily determinable characteristic which may be obtained from empirical observations for given fluids and surfaces. As a point of reference, for webs such as depicted in FIG. 2, average droplet sizes for artificial menstrual fluid (defined below) are typically sufficiently large as to cover at least 2–3 individual capillaries upon initial contact (before acquisition).

Without wishing to be bound by theory, improvements in fluid pass-through characteristics are believed to be received by a reduction in residence time of fluid on the upper surfaces of the web, as well as the movement of fluid from the upper surface into the capillaries for capillary fluid transport. Therefore, it is believed to be desirable for the initial fluid contacting surface of the web to facilitate small-scale movement of fluid (as opposed to larger lateral movement across the web surface) toward the nearest available capillary and then rapidly downward into the underlying structure. The surface energy gradients of the present invention provide the desired Z-direction driving force, as well as the X-Y driving force to impart the desired small-scale fluid movement.

The plurality of small-scale surface energy gradients exhibited by such webs are believed to be beneficial from a fluid-movement perspective. The small-scale gradients aid in the lateral or X-Y movement of fluid droplets formed on the web surface which might otherwise be disposed so as to straddle an intercapillary land area or surface concavity present on the upper web surface where the fluid might otherwise be trapped or at least delayed in its journey toward the nearest available capillary. Accordingly, small scale surface energy gradients on the surface of a capillary web structure preferably have an average spacing which is smaller than the average intercapillary spacing such that they interrupt otherwise constant surface energy land areas between capillaries.

In addition, the regions 98, which are smaller in their surface-wise extent than the typical size of the droplet, stream, or rivulet of bodily fluid incident thereon, subject the droplet, stream, or rivulet of bodily fluid to destabilizing forces due to the inevitability of the fluid bridging a surface energy gradient or discontinuity.

While the surface energy gradients of the type herein described could advantageously be employed on non-capillary structures, including the surfaces of such structures as two-dimensional ("planar") film in accordance with the present invention, it is preferable to employ both small scale X-Y surface energy gradients and small scale Z-direction surface energy gradients of the type herein described to achieve maximum disturbance of fluid and droplet equilibrium and thus minimize fluid residence time and hang-up or residue on the upper regions of the web. Accordingly, the presence of regions 98 may be limited to the first surface of the web, and hence provide X-Y functionality, or limited to the interior of the fluid passageways, but is preferably employed to best advantage both on the first surface of the web and within the fluid passageways.

Accordingly, in capillary web structures of the present invention the surface energy gradients provide a synergistic effect in combination with the capillary nature of the structure to provide enhanced fluid transport and handling characteristics. Fluid on the first surface of the web encounters two differing, complementay driving forces in its journey away from the first surface and toward the second or opposing surface of the web, and typically further onward into the interior of the absorbent article. These two forces likewise combine to oppose fluid movement toward the first surface of the web, thus reducing the incidence of rewet and increasing the surface dryness of the web.

By way of a representative illustration of the synergism of the present invention vis-à-vis the combination or superposition of capillary and surface energy effects, capillary webs according to the present invention have been found to exhibit a unique combination of properties viewed as important from a consumer perspective. More particularly, capillary webs according to the present invention have been found to exhibit good acquisition, dryness, and masking characteristics, which will be defined hereafter.

In general, acquisition is a reflection of the degree to which the fluid transport web does or does not interfere with fluid pass-through. Improved acquisition rates/times reflect little interference or impedance of fluid pass-through, as well as actual influence of fluid driving forces such as capillarity and surface energy gradients. Dryness is a reflection of the degree to which the fluid transport structure resists fluid transport in the opposite direction, in essence, the degree to which the structure acts as a one-way valve for fluid flow in a preferential direction. Masking reflects the cleanliness of the surface after fluid pass-through, further defined as the degree of coloration remaining (with a colored fluid) as well as the size or extend of the discolored region.

Typically, as surface energy of a given capillary web structure decreases uniformly the masking and dryness at the surface improve, but at the expense of a reduction in acquisition characteristics. Conversely, improvements in acquisition realized by a uniform increase in surface energy of a given capillary web structure are typically offset by reduced masking and dryness characteristics. By utilizing the surface energy gradient principles of the present invention, wherein the surface energy of the upper surface is decreased while the surface energy of the lower surface remains higher, and particularly with the preferred orientation and location of the gradients themselves, increases in acquisition, dryness, and/or masking characteristics may be obtained without sacrifices in the remaining parameters. Suitable analytical or test methods for determining web performance with regard to these attributes are described in greater detail in the ANALYTICAL METHODS section below.

A number of physical parameters should be considered in designing a web according to the present invention, more particularly with regard to appropriately sizing and positioning the surface energy gradients for proper fluid handling. Such factors include the magnitude of the surface energy differential (which depends upon the materials utilized), migratability of materials, bio-compatibility of materials, porosity or capillary size, overall web caliper and geometry, surface topography, fluid viscosity and surface tension, and the presence or absence of other structures on either side of the web.

Preferably, the regions 98 of the web 80 have a work of adhesion for water in the range of about 0 erg/cm$^2$ to about 150 erg/cm$^2$, more preferably in the range of about 0 erg/cm$^2$ to about 100 erg/cm$^2$, and most preferably in the range of about 0 erg/cm$^2$ to about 75 erg/cm$^2$. Preferably, the remainder of the web surrounding regions 98 has a work of adhesion for water in the range of about 0 erg/cm$^2$ to about 150 erg/cm$^2$, more preferably in the range of about 25 erg/cm$^2$ to about 150 erg/cm$^2$, and most preferably in the range of about 50 erg/cm$^2$ to about 150 erg/cm$^2$.

Preferably, the difference in the work of adhesion for water between the regions 98 and the remainder of the web is in the range of about 5 erg/cm$^2$ to about 145 erg/cm$^2$, more preferably in the range of about 25 erg/cm$^2$ to about 145 erg/cm$^2$, and most preferably in the range of about 50 erg/cm$^2$ to about 145 erg/cm$^2$.

To manufacture a web such as web 80 depicted in FIG. 2 having surface energy gradients according to the present invention, a sheet of polyethylene is extruded onto a drum where it is vacuum formed into an apertured formed film and then, if desired, is subjected to a corona discharge treatment general in accordance with the teachings of U.S. Pat. No. 4,351,784 issued to Thomas et al. on Sep. 28, 1982; U.S. Pat. No. 4,456,570 issued to Thomas et al. on Jun. 26, 1984; and U.S. Pat. No. 4,535,020 issued to Thomas et al. on Aug. 13, 1985, the disclosures of each of these patents being incorporated herein by reference. The polyethylene may, if desired, have a surfactant incorporated into the resin or topically applied. A surface treatment having a relatively lower surface energy is then applied to the first surface of the apertured formed film to form regions 98 and is preferably cured. A suitable surface treatment is a silicone release coating from Dow Corning of Midland, Mich. available as Syl-Off 7677 to which a crosslinker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively. When such a silicone blend is utililed on a formed film such as depicted in FIGS. 2 and 6, coating application levels of about 0.5 to about 8.0 grams silicone per square meter of web surface area have performed satisfactorily, although other coating levels may prove suitable for certain applications depending upon the nature of the web material and surface, the characteristics of the fluid, etc. The surface energy of the silicone release coating on the first surface of the apertured formed film is less than the surface energy of the polyethylene intermediate portions which may have been subjected to the corona discharge treatment and/or treated with a surfactant.

Other suitable treatment materials include, but are not limited to, fluorinated materials such as fluoropolymers (e.g., polytetrafluoroethylene (PTFE), commercially available under the trade name TEFLON®) and chlorofluoropolymers. Other materials which may prove suitable for providing regions of reduced surface energy include Petrolatum, latexes, paraffins, and the like, although silicone materials are presently preferred for use in fluid-pervious webs in the absorbent article context for their biocompatibility properties. As used herein, the term "biocompatible" is used to refer to materials having a low level of specific adsorption for, or in other words a low affinity for, bio-species or biological materials such as gluco-proteins, blood platelets, and the like. As such, these materials tend to resist deposition of biological matter to a greater extent than other materials under in-use conditions. This property enables them to better retain their surface energy properties as needed for subsequent fluid handling situations. In the absence of biocompatibility, the deposition of such biological material tends to increase the roughness or non-uniformity of the surface, leading to increased drag force or resistance to fluid movement. Consequently, biocompatibility corresponds to reduced drag force or resistance to fluid movement, and hence faster access of fluid to the surface energy gradient and capillary structure. Maintenance of substantially the same surface energy also maintains the original surface energy differential for subsequent or enduring fluid depositions.

Biocompatibility, however, is not synonymous with low surface energy. Some materials, such as polyurethane, exhibit biocompatibility to some degree but also exhibit a comparatively high surface energy. Some low surface energy materials which might otherwise be attractive for use herein, such as polyethylene, lack biocompatibility. Presently preferred materials such as silicone and fluorinated materials advantageously exhibit both low surface energy and biocompatibility.

Suitable surfactants for hydrophilizing or increasing the surface energy of the selected regions of the web to have high surface energy include, for example, ethoxylated esters such as Pegosperse® 200-ML, manufactured by Glyco Chemical, Inc. of Greenwich, Conn., ATMER® 645, manufactured by ICI, glucose amides, tri-block copolymers of ethylene oxide and propylene oxide such as Pluronic® P103, manufactured by BASF, and copolymers of silicone and ethylene glycol such as DC190, manufactured by Dow Coning of Midland, Mich. Surfactants may be incorporated into the starting polymeric material (resin-incorporated surfactant (RIS)) of the web in accordance with the above-referenced and incorporated Published PCT Application WO 93/09741, or alternatively may be applied to the surface of the web by spraying, printing, or other suitable methods such as disclosed in U.S. Pat. No. 4,950,264, issued to Osborn on Aug. 21, 1990, the disclosure of which is hereby incorporated herein by reference.

Alternatively, another approach to generating webs with surface energy gradients according to the present invention involves dip coating the intermediate portion 83 of a corona discharge- and silicone-treated web 80 with a wetting agent (e.g., an aqueous solution of a surfactant such as Pegosperse® 200-ML) such that the intermediate portions 83 have a relatively higher surface energy than the corona discharge- and silicone-treated first surface 81 (regions 98) of the web.

Another preferred method for converting a ribbon of polyethylene film, which may optionally have a surfactant mixed therein, into an apertured formed film is by applying a high pressure fluid jet comprised of water or the like against one surface of the film, preferably while applying a vacuum adjacent the opposite surface of the film Such methods are described in greater detail in commonly assigned U.S. Pat. No. 4,609,518 issued to Curro et al. on Sep. 2, 1986; U.S. Pat. No. 4,629,643 issued to Curro et al. on Dec. 16, 1986; U.S. Pat. No. 4,637,819 issued to Ouellette et al. on Jan. 20, 1987; U.S. Pat. No. 4,681,793 issued to Linman et al. on Jul. 21, 1987; U.S. Pat. No. 4,695,422 issued to Curro et al. on Sep. 22, 1987; U.S. Pat. No. 4,778,644 issued to Curro et al. on Oct. 18, 1988; U.S. Pat. No. 4,839,216 issued to Curro et al. on Jun. 13, 1989; and U.S. Pat. No. 4,846,821 issued to Lyons et al. on Jul. 11, 1989, the disclosures of each of said patents being incorporated herein by reference. The apertured formed film may, if desired, be subjected to a corona discharge treatment. A silicone release coating, may then be applied or printed onto the first surface of the apertured formed film to generate regions 98, and is preferably cured. The intermediate and lower portions of the apertured, formed film web may be dip coated with a wetting agent such that the non-silicone-treated intermediate and lower portions of the web have a relatively higher surface energy than does the corona discharge- and silicone-treated first surface 81 (regions 98) of the web. The surface energy of the silicone-treated regions 98 is less than the surface energy of the untreated portions of the web.

Figure 7:
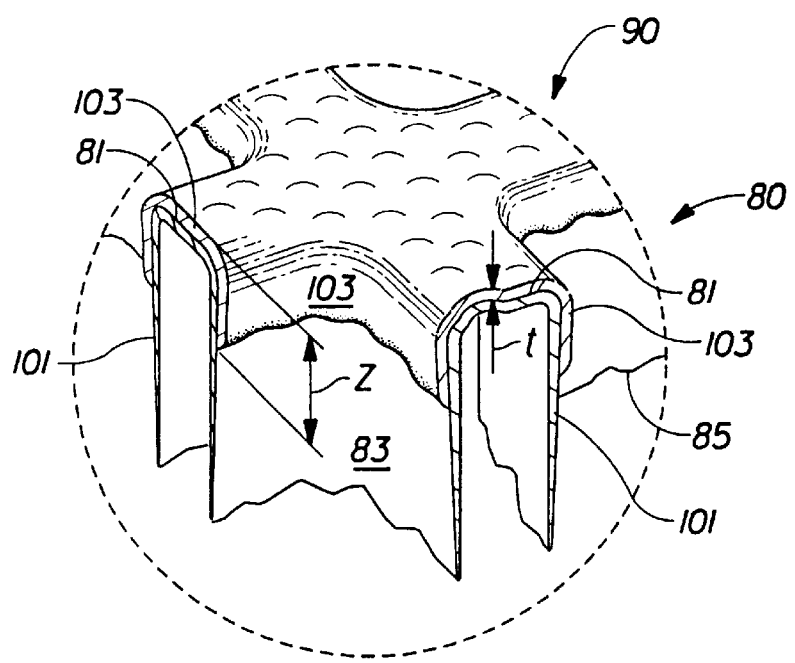
FIG. 7 is a further enlarged, partial view of the web of FIG. 2 illustrating an alternative web construction according to the present invention.

FIG. 7 depicts another method of forming a formed film having a surface energy gradient of the present invention utilizing a multilayer film in a forming process such as described above. The first layer 103 of the film, which will constitute the first surface of the web, is formed of a first material, while the second layer 101 of the film, which will constitute the second surface of the web, is formed of a second material. The second material preferably exhibits a greater ductility and a higher surface energy than the second material, so that during the aperturing process, the first layer 103 of the film fractures first while the second layer 101 of the film stretches to a greater extent to form the lower portion of the web. The first surface of the finished web is thus comprised of the first material, while the intermediate and lower portions of the finished web are comprised of the second material exposed following the fracture of the first material, with a boundary between the two materials located in the capillaries and slightly below the first surface of the web as illustrated in FIG. 7.

The finished web thus exhibits a surface energy gradient from the first surface to the second surface defined by the interface between the edge of the first layer 103 (a "region" corresponding to those of FIG. 6) without the additional steps of treating the first, intermediate, and/or second surfaces with additives or coatings. Note in FIG. 7 the irregularity of the edge of the first layer 103, which corresponds to a random distance of the surface energy gradient (defined by the edge of the region 103) from the first surface of the web. The first and second layers herein described may be separated from one another by one or more intervening layers in a multilayer film (not shown) having 3 or more layers which may optionally participate in the surface energy gradient of the film by having surface energy characteristics intermediate those of the uppermost and lowermost layers.

Figure 8:
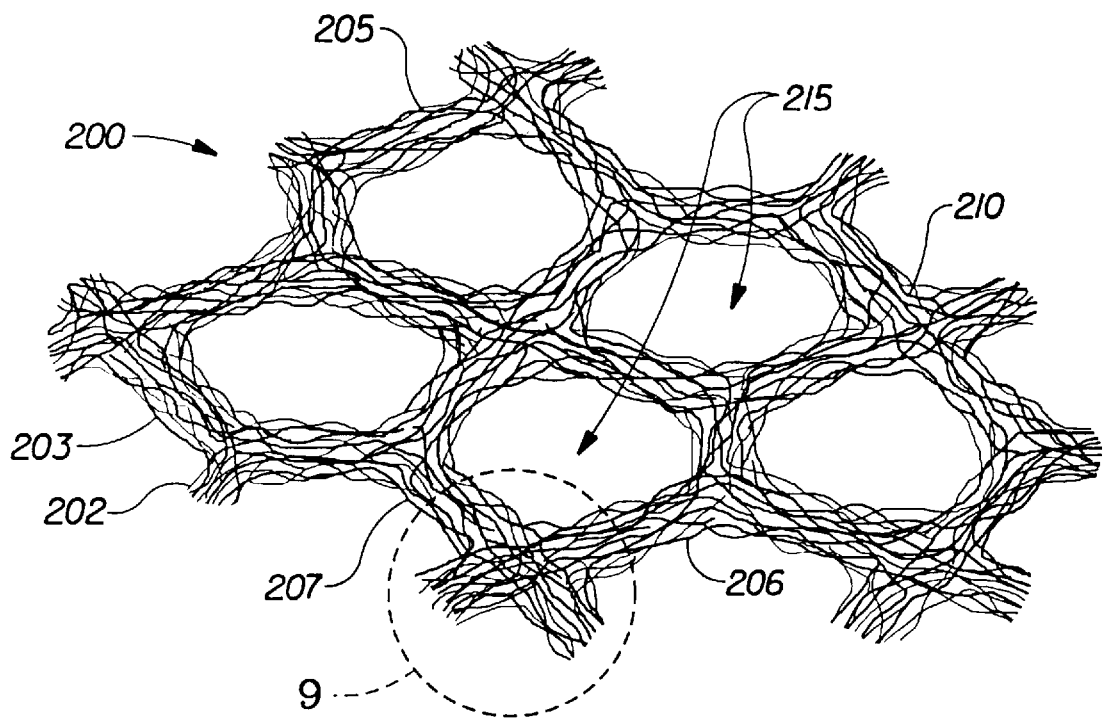
FIG. 8 is an enlarged, partially segmented, perspective illustration of a nonwoven web illustrating another preferred embodiment according to the present invention.
Figure 9:
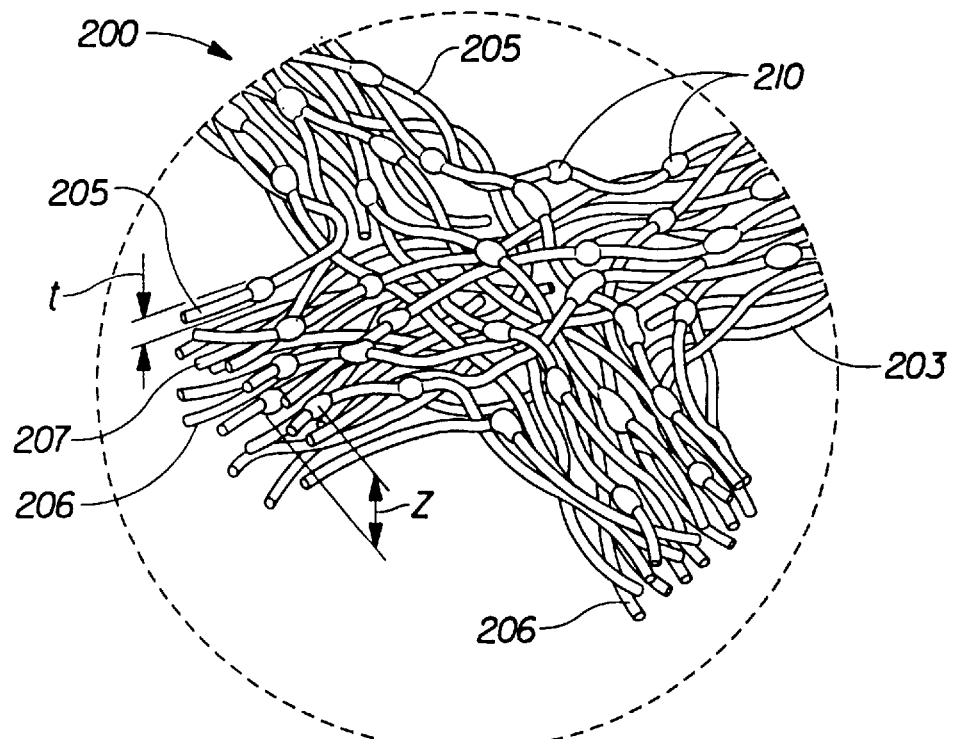
FIG. 9 is a further enlarged, partial view similar to FIG. 6 of the nonwoven web of FIG. 8.

Referring now to FIGS. 8 and 9 there is shown a perspective view of another embodiment of a fluid transport web 200 in accordance with the present invention. Fluid transport web 200 includes a fluid pervious nonwoven web 202 which is preferably comprised of polypropylene fibers 203. Other suitable fibers include natural fibers such as wood, cotton, or rayon, or synthetic fibers such as polyester or polyethylene, bi-component fibers, or combinations of natural and synthetic fibers, as well as various paper, tissue, or paper-like fibrous materials.

The nonwoven web 202 preferably has a first or upper surface 205 and a second surface or lower 206. The first surface 205 is spaced from the second surface 206 by an intermediate portion 207. The first surface 205 preferably has a plurality of regions 210 thereon corresponding to regions 98 depicted in FIG. 6. Preferably, the regions 210 exhibit a comparatively low surface energy and preferably comprise a low surface energy surface treatment such as described above with regard to the embodiment of FIGS. 2 and 6. A plurality of apertures 215 preferably extend from the first surface 205 to the second surface 206 of the nonwoven web 202.

Preferably, the regions 210 have a relatively low surface energy and a relatively low work of adhesion as compared to the fibers of the nonwoven which have a relatively high surface energy and a relatively high work of adhesion. Accordingly, the treated nonwoven web 200 exhibits a plurality of surface energy gradients defined by the boundaries of regions 210, i.e., the interfaces between regions 210 and the surrounding fiber surfaces.

Surface treatments for generating regions 210 may be applied to the first surface 205 of the nonwoven web 202 by techniques known in the art such as screen printing, gravure printing, spraying, dip coating, etc. The nonwoven web 200 may be apertured by techniques known in the art such as needle punching, hydroentangling, ringrolling (rolling between interengaged, corrugated rolls), slitting and tentering, embossing, etc.

For configurations wherein the web has defined apertures, the surface treatment 210 is preferably applied to the first surface of the nonwoven web after the aperturing operation is complete. Alternatively, the surface treatment 210 may be applied to the first surface of the nonwoven web prior to the aperturing operation.

As depicted in FIG. 9, the relationship of the regions 210 to the surface topography (including individual fibers protruding upward from the upper surface of the web) is believed to be an important aspect of the present invention. Note the intermittent or discontinuous, spaced nature of the regions with regard to the surface direction of the web and the thickness direction of the web, particularly since the surface treatment as depicted in FIG. 9 is actually a plurality of discrete particles, droplets, or globules which coat portions of individual fibers rather than a bridging or is masking of the fibers which would occlude the interfiber pores. As discussed above, this discontinuity results in the generation of a plurality of small-scale surface energy gradients which are believed to be beneficial from a fluid-movement perspective.

Also clearly depicted in FIG. 9 is the penetration of the surface treatment into and below the first surface 205 of the nonwoven web 202. While the majority of the regions 210 are concentrated near the first surface 205 itself the treated regions extend downward through the web on a fiber-by-fiber basis to achieve a penetration analogous to that defined above with respect to the formed film web. Preferably, regions 210 are concentrated near the first surface 205 and decrease in frequency (increase in spacing) with increasing distance from the first surface, such that more low surface energy regions, and hence more surface energy gradients, are generated at or near the first surface 205 for greater effect on fluids on or near the first surface. On average, therefore, the upper regions of the web near the first surface would exhibit a lower average surface energy than that exhibited by lower regions of the web nearer to the second surface.

Although the foregoing discussion has focused on the presently preferred apertured nonwoven structure having discrete apertures comparatively large in relation to the interfiber spacing, the principles of the present invention are believed to be applicable with equal effect to non-apertured nonwoven structures with sufficient effective porosity to permit the desired fluid pass-through characteristics. This applicability is believed to be due to the non-occlusion of the interfiber capillaries such that sufficient fluid passageways remain open for fluid transmission to the underlying structure. In a structure having discrete apertures comparatively large in relation to the interfiber spacing, non-occlusion is less important but still believed to be advantageous.

Although the foregoing discussion has focused on a true nonwoven substrate, it should be understood that the concepts of the present invention could be applied to woven or hybrid woven/nonwoven substrates in similar fashion. In doing so, recognition of the degree of porosity present in the interwoven structure is necessary to extrapolate the foregoing discussion regarding the porosity and interfiber capillary spacing of the nonwoven webs to interwoven structures.

In addition, the definition of "fiber" as utilized herein is intended to also encompass a type of fiber structure commonly referred to as a "capillary channel fiber", that is, a fiber having a capillary channel formed therein. Suitable fibers of this variety are described in greater detail in U.S. Pat. Nos. 5,200,248, 5,242,644, and 5,356,405, all of which issued to Thompson et al. on Apr. 6, 1993, Sep. 7, 1993, and Oct. 18, 1994, respectively, the disclosures of which are hereby incorporated herein by reference. Fibrous structures formed of such fibers may exhibit not only inter-fiber capillaries and spaces, but also intra-fiber capillary structures.

Figure 10:
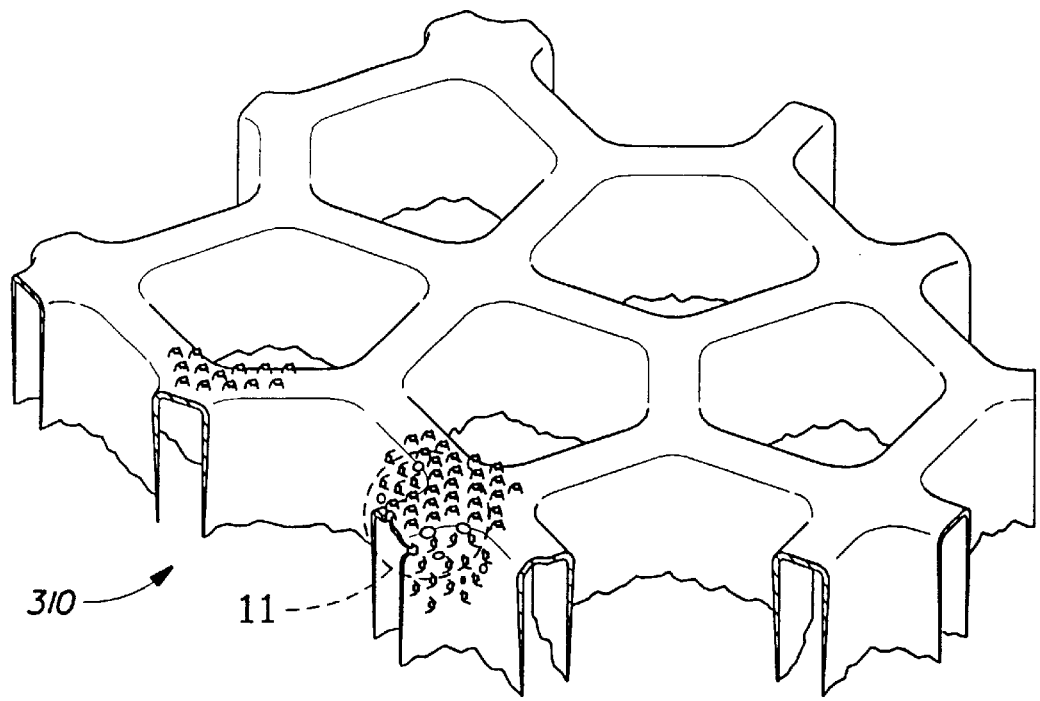
FIG. 10 is a greatly enlarged simplified schematic cross-sectional illustration similar to FIG. 2 of a macroscopically expanded, microscopically apertured three-dimensional web exhibiting a surface energy gradient according to the present invention.

FIG. 10 is an enlarged partially segmented, perspective illustration of a three-dimensional, fluid-pervious formed-film web embodiment of the present invention, generally indicated as 310. The geometrical configuration of the fluid pervious web 310 is generally similar to that of FIG. 2, but including microapertures in accordance with commonly assigned U.S. Pat. No. 4,629,643, issued Dec. 16, 1986 to Curro and Linman, the disclosure of which is hereby incorporated herein by reference.

Figure 11:
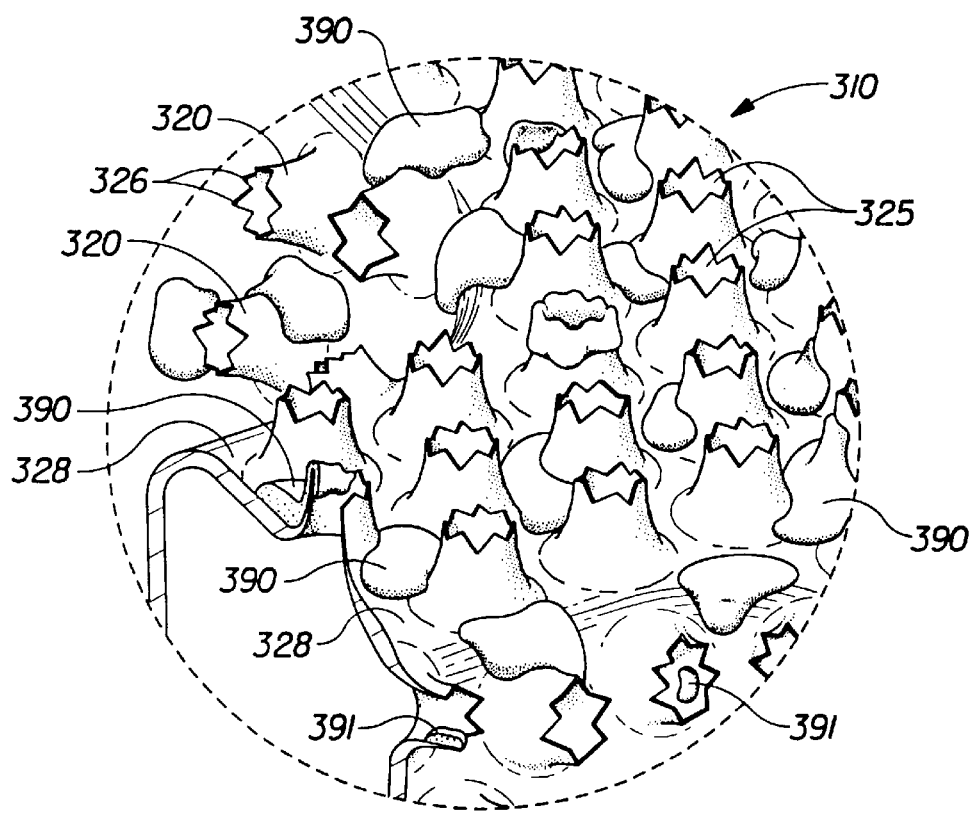
FIG. 11 is a further enlarged, partial view similar to FIG. 6 of the web of FIG. 10.

FIG. 11 is an enlarged partial view of the web of FIG. 10, depicting in greater detail the relationship of the microapertures 325 to the overall web structure. Also depicted in FIG. 11 is the primary undeformed web surface or lands 328 between and around the bases of the microscopic surface aberrations, 320 which culminate in microapertures 325 having petals 326. FIG. 11 also depicts the presence of discrete, discontinuous, spaced regions 390 which preferably exhibit a comparatively low surface energy compared with intervening surfaces of the web in similar manner, fashion, and composition to those depicted in FIG. 6.

Figure 12:
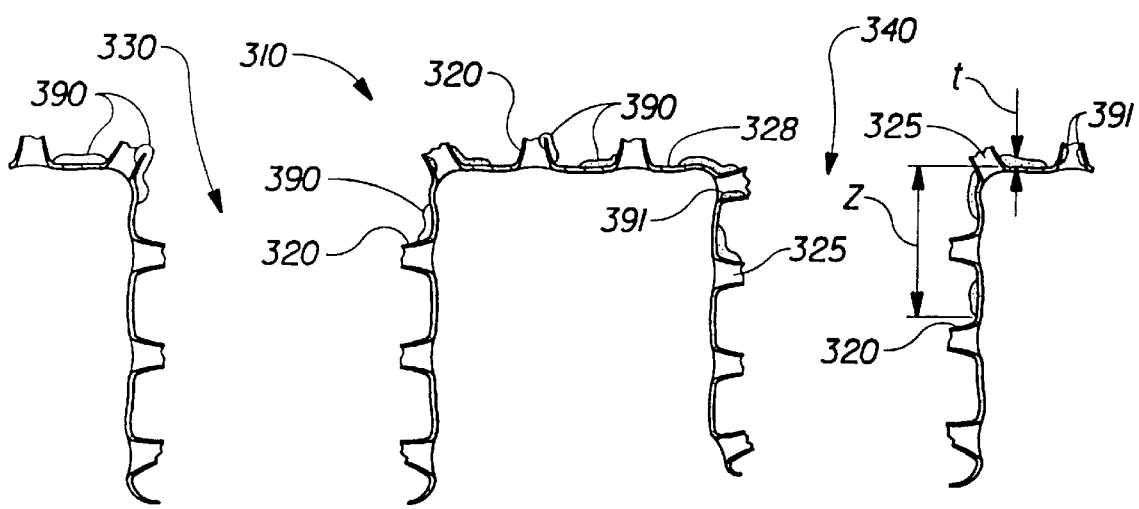
FIG. 12 is an enlarged, cross-sectional view of the web of FIGS. 10 and 11, but showing in greater detail the orientation of the surface energy gradients in relation to the web.

FIG. 12 is a cross-sectional view of one of the macroscopic structures of FIG. 11, more clearly depicting the presence of regions 390 on the upper surface of the structure. As shown in FIG. 12, under some circumstances the regions 390 may at least enter the interior of at least some of the nicroapertures 325 (as indicated at 391). This tends to further reduce the surface energy of the upper surface of the web in comparison with the intermediate portion having unobstructed microapertures. In addition, partial or total coverage of the interior of microapertures on the uppermost portion of the formed film with the regions of low surface energy further reduce the likelihood that fluid will be trapped inside the microapertures, thus enhancing the feeling of dryness experienced by the wearer.

As depicted in FIGS. 11–12, the relationship of the regions 390 to the surface topography (including microapertures 325) is believed to be an important aspect of the present invention. Note the intermittent or discontinuous nature of the regions 390 with regard to the surface direction of the web. As discussed above, this results in the generation of a plurality of small-scale surface energy gradients at the interface between each of such regions and the surrounding web surface which are believed to be beneficial from a fluid-movement perspective.

Also depicted in FIG. 12 is the penetration of the regions 390 below the surface of the web and down into the apertures analogously to the discussion of the penetration above. FIG. 12 also depicts different levels or degrees of penetration of the regions 390 into the macroapertures of the web, with macroaperture 330 exhibiting comparatively little penetration below the first surface of the web and with macroaperture 340 exhibiting a greater degree of penetration. Preferably, regions 390 are concentrated near the first surface and decrease in frequency (increase in spacing) with increasing distance from the first surface, such that more low surface energy regions, and hence more surface energy gradients, are generated at or near the first surface for greater effect on fluids on or near the first surface. On average, therefore, the upper regions of the web near the first surface would exhibit a lower average surface energy than that exhibited by lower regions of the web nearer to the second surface.

More specific details as to the nature of the processes which may be utilized to manufacture the microapertured, macroscopically expanded and/or apertured formed films depicted in FIGS. 10–12 are set forth in conunonly assigned U.S. Pat. No. 4,609,518, issued Sep. 2, 1986 to Curro et al., the disclosure of which is hereby incorporated herein by reference. Following manufacture of the microapertured formed films, the surface energy gradient properties of the present invention are imparted to the formed films in the manner described above with respect to FIGS. 2 and 6, and they may be incorporated into absorbent articles such as those depicted in FIGS. 14 and 15. Indeed, the surface energy gradient properties of the present invention are particularly useful in combating the tendency of fluids to accumulate in and around the microstructures present in formed films such as depicted in FIGS. 10–12. This leads to webs having improved clothlike characteristics without sacrificing apparent consumer dryness.

While much of the foregoing discussion has focused on unitary (one structural element in the Z-direction) fluid pervious webs of a single lamina or layer of material, it is to be understood that the principles of the present invention are believed equally applicable to unitary (one structural element in the Z-direction) fluid pervious webs of multiple laminae or layers which have been joined into a composite structure. Whether such multi-laminae structures are of multiple layers of materials of similar physical characteristics (i.e., plural film layers, plural woven layers, or plural nonwoven layers), such structures may also include the family of hybrid materials comprising layers from diverse physical families of materials, such as nonwoven/film composites, nonwoven/film/nonwoven composites, etc. In the case of such materials, the surface energy gradient principles of the present invention are believed to be applicable to the surfaces of the resulting structure presented to the fluid in the same fashion as that hereinabove described for the respective material in isolation.

Figure 13:
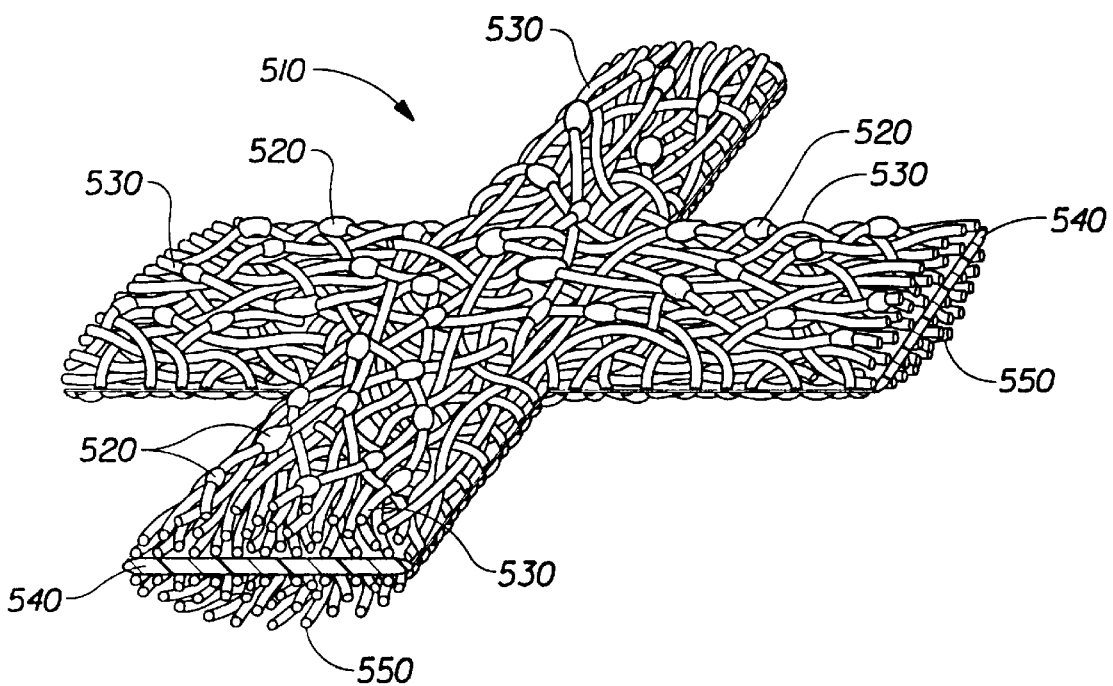
FIG. 13 is a view generally similar to that of FIG. 9, but illustrating a further embodiment of a composite web according to the present invention.

As an illustrative example of this aspect of the present invention, FIG. 13 illustrates a nonwoven/film/nonwoven composite 510 wherein a nonwoven surface is presented to the wearer as well as the incoming bodily fluid. A representative composite of this variety is described in greater detail in U.S. Pat. No. 4,780,352, issued Oct. 25, 1988 to Palumbo, the disclosure of which is hereby incorporated herein by reference. Such a composite web in accordance with the present invention comprises an upper fibrous layer 530, an intermediate plastic film layer 540, and a lower fibrous layer 550. Accordingly, the surface energy gradient principles of the present invention, embodied in the regions 520 on, in, and around the fibers of the upper fibrous layer 530, are structurally and behaviorally similar in nature to that of the nonwoven web illustrated and described above with regard to FIGS. 8 and 9. In addition, the plastic film layer 540 may function as a barrier to further penetration of surface treatments utilized to generate regions 520, thus ensuring their concentration near the upper surface of the web. Conversely, if the upper surface of the composite web were a film with an underlying fibrous layer, the surface energy gradient principles of the present invention would be structurally and behaviorally similar in nature to that of the formed film web illustrated and described above with regard to FIGS. 6, 7, 11, and 12. Accordingly, it is believed that underlying strata in a composite structure, while participating in overall web characteristics, would not influence fluid transfer behavior of the initial fluid acquisition insofar as they do not constitute an exposed surface to the incoming fluid.

Other suitable materials include polymeric foam materials comprising a hydrophilic flexible network of interconnected open spaces as a fluid transport web, to which may be imparted the surface energy gradients of the present invention. Suitable foam materials of this variety are described in U.S. Pat. No. 5,147,345, issued Sep. 15, 1992 to Young et al., and U.S. Pat. No. 5,397,316, issued Mar. 14, 1995 to LaVon et al., the disclosures of which are hereby incorporated herein by reference.

In addition to the formation processes described above, the surface energy gradients according to the present invention may be applied to film, nonwoven, or composite structures which have been subjected to other mechanical processes, such as creping, straining/activation by rolling with corrugated rolls or otherwise. Such mechanical process may be either alternative to the processes described hereinabove or in addition to such processes, i.e., sequentially either before or after such processes.

While much of the foregoing discussion has focused on the presently preferred approach of beginning with a predominantly hydrophilic web and applying a coating, treatment, or overlying layer of material to generate low surface energy regions and to render the upper portions hydrophobic, it is to be understood that other approaches to generating surface energy gradients are contemplated as well and are within the scope of the present invention. Such approaches would include applying a hydrophilic material (e.g., a hydrophilic latex) to the lower portions of an originally hydrophobic web to generate hydrophilic regions with boundaries at interfaces with hydrophobic web surfaces, forming the web of two or more materials of diverse surface energy characteristics with surface energy gradients formed by boundaries between the respective materials, forming the web of a material predominantly hydrophobic or predominantly hydrophilic and altering the surface chemistry of selected regions thereof by mechanical, electromagnetic, or chemical bombardment or treatment techniques know in the art to thus generate selective surface energy gradients, preferential migration of chemical web components capable of surface energy alteration, treating hydrophobic regions to be temporarily hydrophilic and reveal surface energy gradients in use, etc.

REPRESENTATIVE ABSORBENT ARTICLE

As used herein, the term "absorbent article" refers generally to devices used to absorb and contain body exudates, and more specifically refers to devices which are placed against or in proximity to the body of the wearer to absorb and contain the various exudates discharged from the body. The term "absorbent article" is intended to include diapers, catamenial pads, tampons, sanitary napkins, incontinent pads, and the like, as well as bandages and wound dressings. The term "disposable" is used herein to describe absorbent articles which are not intended to be laundered or otherwise restored or reused as an absorbent article (i.e., they are intended to be discarded after limited use, and, preferably, to be recycled, composted or otherwise disposed of in an environmentally compatible manner). A "unitary" absorbent article refers to absorbent articles which are formed as a single structure or as separate parts united together to form a coordinated entity so that they do not require separate manipulative parts such as a separate holder and pad.

A preferred embodiment of a unitary disposable absorbent article made in accordance herewith is the catamenial pad, sanitary napkin 20, shown in FIG. 14. As used herein, the term "sanitary napkin" refers to an absorbent article which is worn by females adjacent to the pudendal region, generally external to the urogenital region, and which is intended to absorb and contain menstual fluids and other vaginal discharges from the wearers body (e.g., blood, menses, and urine). Interlabial devices which reside partially within and partially external to the wearer's vestibule are also within the scope of this invention. It should be understood, however, that the present invention is also applicable to other feminine hygiene or catamenial pads, or other absorbent articles such as diapers, incontinent pads, and the like, as well as other webs designed to facilitate fluid transport away from a surface such as disposable towels, facial tissues, and the like.

It is to be understood that the overall size, shape, and/or configuration of the absorbent article, if any, into which fluid transport webs according to the present invention are incorporated, or utilized in conjunction with, have no criticality or functional relationship to the principles of the present invention. Such parameters, however, must be considered along with the intended fluid and intended functionality when determining appropriate web configurations and appropriate orientation of surface energy gradients according to the present invention.

Sanitary napkin 20 is illustrated as having two surfaces such as first surface 20a, sometimes referred to as a wearer-contacting or facing surface, a body-contacting or facing surface or "body surface", and second surface 20b, sometimes referred to as a garment-facing or contacting surface, or "gament surface". The sanitary napkin 20 is shown in FIG. 14 as viewed from its first surface 20a. The first surface 20a is intended to be worn adjacent to the body of the wearer. The second surface 20b of the sanitary napkin 20 (shown in FIG. 15) is on the opposite side and is intended to be placed adjacent to the wearers undergarment when the sanitary napkin 20 is worn The sanitary napkin 20 has two centerlines, a longitudinal centerline "L" and a transverse centerline "T". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable and refer to a line, axis or direction which lies within the plane of the sanitary napkin 20 that it generally perpendicular to the longitudinal direction. FIG. 14 also shows that the sanitary napkin 20 has a periphery 30 which is defined by the outer edges of the sanitary napkin 20 in which the longitudinal edges (or "side edges") are designated 31 and the end edges (or "ends") are designated 32.

FIG. 14 is top plan view of a sanitary napkin 20 of the present invention in a substantially flat state with portions of the sanitary napkin being cut away to more clearly show the construction of the sanitary napkin 20 and with the portion of the sanitary napkin 20 which faces or contacts the wearer 20a oriented towards the viewer. As shown in FIG. 14, the sanitary napkin 20 preferably comprises a liquid pervious topsheet 22, a liquid impervious backsheet 23 joined with the topsheet 22, an absorbent core 24 positioned between the topsheet 22 and the backsheet 23, and a secondary topsheet or acquisition layer 25 positioned between the topsheet 22 and the absorbent core 24.

The sanitary napkin 20 preferably includes optional side flaps or "wings" 34 that are folded around the crotch portion of the wearer's panty. The side flaps 34 can serve a number of purposes, including, but not limited to helping to hold the napkin in proper position while protecting the wearers panty from soiling and keeping the sanitary napkin secured to the wearer's panty.

FIG. 15 is a cross-sectional view of the sanitary napkin 20 taken along section line 15—15 of FIG. 14. As can be seen in FIG. 15, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

The topsheet 22 has a first surface 22a and a second surface 22b positioned adjacent to and preferably secured to a first surface 25a of the fluid acquisition layer 25 to promote fluid transport from the topsheet to the acquisition layer. The second surface 25b of the acquisition layer 25 is positioned adjacent to and is preferably secured to the first surface 24a of an absorbent core or fluid storage layer 24 to promote fluid transport from the acquisition layer to the absorbent core. The second surface 24b of the absorbent core 24 is positioned adjacent to and is preferably secured to the first surface 23a of the backsheet 23.

In addition to having a longitudinal direction and a transverse direction, the sanitary napkin 20 also has a "Z" direction or ais, which is the direction proceeding downwardly through the topsheet 22 and into whatever fluid storage layer or core 24 that may be provided. The objective is to provide a substantially continuous path between the topsheet 22 and the underlying layer or layers of the absorbent article herein, such that fluid is drawn in the "Z" direction and away from the topsheet of the article and toward its ultimate storage layer.

The absorbent core 24 may be any absorbent means which is capable of absorbing or retaining liquids (e.g., menses and/or urine). As shown in FIGS. 14 and 15, the absorbent core 24 has a body surface 24a, a garment facing surface 24b side edges, and end edges. The absorbent core 24 may be manufactured in a wide variety of sizes and shapes (e.g. rectangular, oval, hourglass, dogbone, asymmetric, etc.) and from a wide variety of liquid-absorbent materials commonly used in sanitary napkins and other absorbent articles such as communicative wood pulp which is generally referred to as airfelt. Examples of other suitable absorbent materials include creped cellulose wadding; meltblown polymers including conform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these.

The configuration and construction of the absorbent core may also be varied (e.g., the absorbent core may have varying caliper zones (e.g. profiled so as to be thicker in the center), hydrophilic gradients, superabsorbent gradients or lower density or lower average basis weight acquisition zones; or may comprise one or more layers or structures). The total absorbent capacity of the absorbent core, should, however, be compatible with the design loading and the intended use of the absorbent article. Further, the size and absorbent capacity of the absorbent core may be varied to accommodate different uses such as incontinent pads, pantiliners, regular sanitary napkins, or overnight sanitary napkins.

Exemplary absorbent structures for use as the absorbent core in the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, the Procter & Gamble Company, published Oct. 22, 1986 in the name Duenk, et al. The disclosures of each of these patents are incorporated herein by reference.

A preferred embodiment of the absorbent core 24 has a surface energy gradient similar to the surface energy gradient of the topsheet 22. The body facing surface 24a of the absorbent core and the portion of the absorbent core 24 immediately adjacent the body facing surface 24a preferably has a relatively low surface energy as compared to the garment facing surface 24b which has a relatively high surface energy. It is important to note that while there is a surface energy gradient within the absorbent core 24, the surface energy of the wearer-contacting or the body facing surface 24a of the absorbent core is preferably greater than the surface energy of the garment facing surface 25b of the acquisition layer 25. This relationship is preferred in order that fluid may be pulled or driven from the acquisition layer into the absorbent core. If the surface energy of the body facing surface 24a of the absorbent core were less than that of the garment facing surface 25b of the acquisition layer fluid in the acquisition layer 25 would be repelled by the absorbent core, thus rendering the absorbent core useless.

The backsheet 23 and the topsheet 22 are positioned adjacent the garment facing surface and the body facing surface respectively of the absorbent core 24 and are preferably joined thereto and to each other by attachment means (not shown) such as those well known in the art. For example, the backsheet 23 and/or the topsheet 22 may be secured to the absorbent core or to each other by a uniform continuous layer of adhesive, a patterned layer of adhesive or any array of separate lines, spirals or spots of adhesive. Adhesives which have been found to be satisfactory are manufactured by H.B. Fuller Company of St. Paul, Minn. under the designation HL-1258, and by Findlay of Minneapolis, Minn., under the designation H-2031. The attachment means will preferably comprise an open pattern network of filaments of adhesive as disclosed in U.S. Pat. No. 4,573,986 issued to Minetola et al. on Mar. 4, 1986, the disclosure of which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978 and U.S. Pat. No. 4,842,666 issued to Werenicz on Jun. 27, 1989. The disclosures of each of these patents are incorporated herein by reference. Alternatively, the attachment means may comprise heat bonds, pressure bonds, ultrasonic bonds, dynamic mechanical bonds or any other suitable attachment means or combinations of these attachment means as are known in the art.

The backsheet 23 is impervious to liquids (e.g., menses and/or urine) and is preferably manufactured from a thin plastic film, although other flexible liquid impervious materials may also be used. As used herein, the term "flexible" refers to materials which are compliant and are more readily conformed to the general shape and contours of the human body. The backsheet 23 prevents the exudates absorbed and contained in the absorbent core from wetting articles which contact the sanitary napkin 20 such as pants, pajamas and undergarments. The backsheet 23 may thus comprise a woven or nonwoven material polymeric films such as thermoplastic films of polyethylene or polypropylene, or composite materials such as a film-coated nonwoven material. Preferably, the backsheet of the polyethylene film having a thickness of from about 0.012 mm (0.5 mil) to about 0.051 mm (2.0 mil). Exemplary polyethylene films are manufactured by Clopay Corporation of Cincinmati, Ohio, under the designation P18-1401 and by Tredegar Film Products of Terre Haute, Ind., under the designation XP-9818. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means or attachment means (not shown) well-known for such purposes. Preferably, the sanitary napkin is placed in the users undergarment or panty and secured thereto by a fastener such as an adhesive. The adhesive provides a means for securng the sanitary napkin in the crotch portion of the panty. Thus, a portion or all of the outer or garment facing surface 23b of the backsheet 23 is coated with adhesive. Any adhesive or glue used in the art for such purposes can be used for the adhesive herein, with pressure-sensitive is adhesives being preferred. Suitable adhesives are manufactured by H B. Fuller Company of St. Paul, Minn., under the designation 2238. Suitable adhesive fasteners are also described in U.S. Pat. No. 4,917,697. Before the sanitary napkin is placed in use, the pressure-sensitive adhesive is typically covered with a removable release liner 37 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. A non-limiting example of a suitable release finer is BL30MG-A Silox 4P/O, which is manufactured by the Akrosil Corporation of Menasha, Wis. The sanitary napkin 20 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps 34 each of which are adjacent to and extend laterally from the side edge of the absorbent core. The flaps 34 are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; and U.S. Pat. No. 4,589,876 entitled "Sanitary Napkin", which issued to Van Tilburg on May 20, 1986. The disclosure of each of these patents is hereby incorporated herein by reference.

In a preferred embodiment of the present invention, an acquisition layer(s) 25 may be positioned between the topsheet 22 and the absorbent core 24. The acquisition layer 25 may serve several functions including improving wicking of exudates over and into the absorbent core. There are several reasons why the improved wicking of exudates is important, including providing a more even distribution of the exudates is throughout the absorbent core and allowing the sanitary napkin 20 to be made relatively thin. The wicking referred to herein may encompass the transportation of liquids in one, two or all directions (i.e., in the x-y plane and/or in the z-direction). The acquisition layer may be comprised of several different materials including non-woven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. The disclosures of each of these references are hereby incorporated herein by reference. In a preferred embodiment, the acquisition layer may be joined with the topsheet by any of the conventional means for joining webs together, most preferably by fusion bonds as is more fidly described in the above-referenced Cree application.

In a preferred embodiment the acquisition layer 25 preferably has a surface energy gradient similar to that of the topsheet 22 and/or absorbent core 24. In a preferred embodiment, the first or wearer-facing surface 25a preferably has a relatively low surface energy as compared to the absorbent pad contacting surface 25b. Preferably, the surface energy of the first surface 25a of the acquisition layer 25 is preferably greater than the surface energy of the second surface of the topsheet 22. Furthermore, the second surface of the acquisition layer 25b has a relatively low surface energy compared to the surface energy of the body facing surface 24a of the absorbent core 24.

Figure 16:
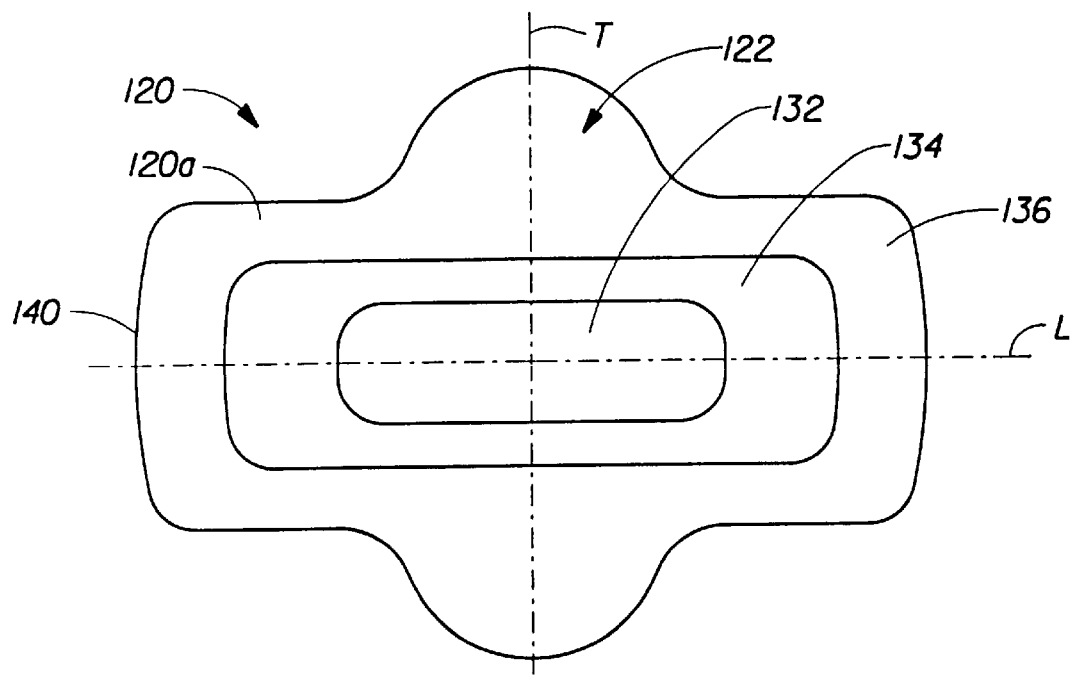
FIG. 16 is a top plan view of the topsheet portion of a sanitary napkin embodiment made according to the present invention.

Referring now to FIG. 16 there is shown another preferred embodiment of a sanitary napkin 120 made according to the present invention. The sanitary napkin 120 is shown in FIG. 16 as viewed from its first or wearer-contacting surface 120a. The sanitary napkin 120 includes a liquid pervious topsheet 122, a liquid impervious backsheet (not shown), joined with the topsheet 122, an absorbent core (not shown), positioned between the topsheet 122 and the backsheet, and an acquisition layer (not shown) positioned between the topsheet 122 and the absorbent core.

The topsheet 122 preferably includes a plurality of regions and/or zones, such as a first central region 132, a second region 134 adjacent to and contiguous with the first region 132, and a third region 136 adjacent to and contiguous with the second region 134. Preferably, the first surface of the topsheet 122 within the first central region 132 has a relatively higher surface energy than that of the topsheet 122 within the adjacent second region 134. Likewise, the first surface of the topsheet 122 within the second region 134 has a relatively higher surface energy than that of the topsheet 122 within the adjacent third region 136. Thus, fluid deposited on the topsheet 122 will be driven from the third region 136 toward the second region 134 and from the second region 134 toward the first region 132. Accordingly, fluid will be directed from the third region 136 towards the first region 132 of the topsheet 122 to help prevent any run-off of fluids over the periphery 140 of the sanitary napkin.

While the first or wearer-contacting surface of the topsheet 122 has a surface energy gradient from region to region, which may be discrete or continuous, the topsheet 122 will also preferably have an additional surface energy gradient between the first surface and the sidewall or intermediate portions of the topsheet 122. The surface energy of the sidewall portions 134 within the respective regions of the topsheet, will be higher than the surface energy of the wearer-contacting surface in the first, second and third regions of the topsheet 122. Thus, the topsheet will also promote the transmission of fluids in the "Z" direction similar to that of web 80 disclosed in FIG. 2.

In some situations it may be desirable to have a surface energy gradient on the first surface of the topsheet 122 which forces fluid from the first region to the second region, and from the second region to the third region. In such an embodiment, the first surface of the topsheet 122 within the first region 132 has a relatively lower surface energy than that of the topsheet 122 within the adjacent second region 134. Similarly, the first surface of the topsheet 122 within the second region 134 has a relatively lower surface energy than that of the topsheet 122 within the adjacent third region 136. Thus, fluid deposited on the topsheet 122 will be driven from the first region 132 toward the second region 134, and from the second region 134 toward the third region 136. This type of surface energy gradient may be desirable when trying to fully utilize the absorbent capacity of the underlying absorbent core by spreading bodily fluids across the first surface of the topsheet, the fluids will have a more direct path to the peripheral portions of the underlying absorbent core.

The regions or zones 132, 134, 136 are shown in FIG. 16 as generally being of an oval configuration. However, the regions may be formed in a wide variety of shapes and sizes, such as rectangular, elliptical, hourglass, dogbone, asymmetric, triangular, circular, etc., or even random shapes and sizes.

Figure 17:
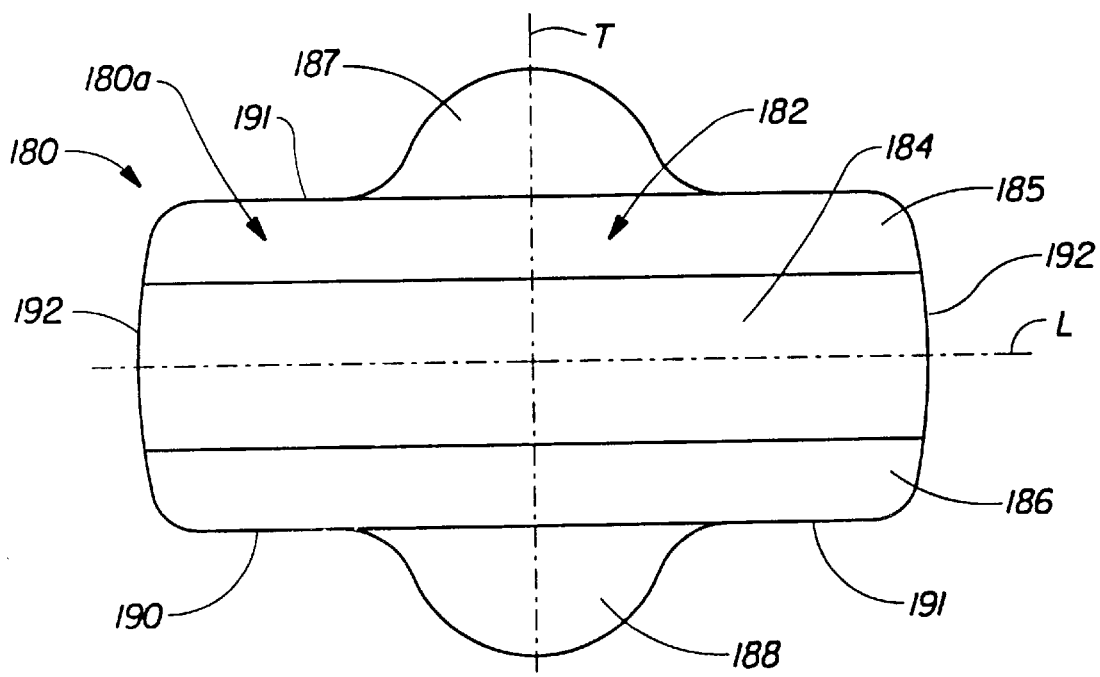
FIG. 17 is a top plan view of the topsheet portion of another sanitary napkin embodiment made according to the present invention.

Referring now to FIG. 17 there is shown a sanitary napkin 180 as viewed from its first surface 180a. The sanitary napkin 180 includes elements or components similar to that of sanitary napkin 20 shown in FIGS. 14 and 15 such as a liquid pervious topsheet 182, a liquid impervious backsheet joined with the topsheet 182, an absorbent core positioned between the topsheet 182 and the backsheet, and a secondary topsheet or acquisition layer positioned between the topsheet 182 and the absorbent core. The sanitary napkin 180 has a periphery 190 which is defined by the outer edges of the sanitary napkin 180 in which the longitudinal edges (or "side edges") are designated 191 and the end edges (or "ends") are designated 192.

The topsheet 182 includes a plurality of regions extending generally parallel to the longitudinal axis "L" of the sanitary napkin 180, and includes a first or central region 184 extending parallel to the longitudinal axis from one end of the sanitary napkin to the other end. Adjacent to the first or central region 184 is a pair of second regions 185, 186 extending essentially parallel to the first region 184. Adjacent the second regions 185, 186, respectively, are a pair of third regions 187, 188. Preferably, the first region has a relatively high surface energy as compared to the second regions 185, 186. Similarly, the second regions 185, 186 have a relatively high surface energy as compared to the third regions 187, 188.

Alternatively, the first region may have a relatively low surface energy as compared to the second regions 185, 186. The second regions 185, 186 may then have a relatively low surface energy as compared to the third regions 187, 188.

It should be noted that the surface energy characteristics of the regions depicted in FIGS. 16 and 17 are in addition to the surface energy gradients and characteristics of the present invention. Accordingly, within one or more of the defined regions in FIGS. 16 and 17 the surface energy features and characteristics described in FIGS. 2 and 6–13 are included therein as well.

Figure 18:
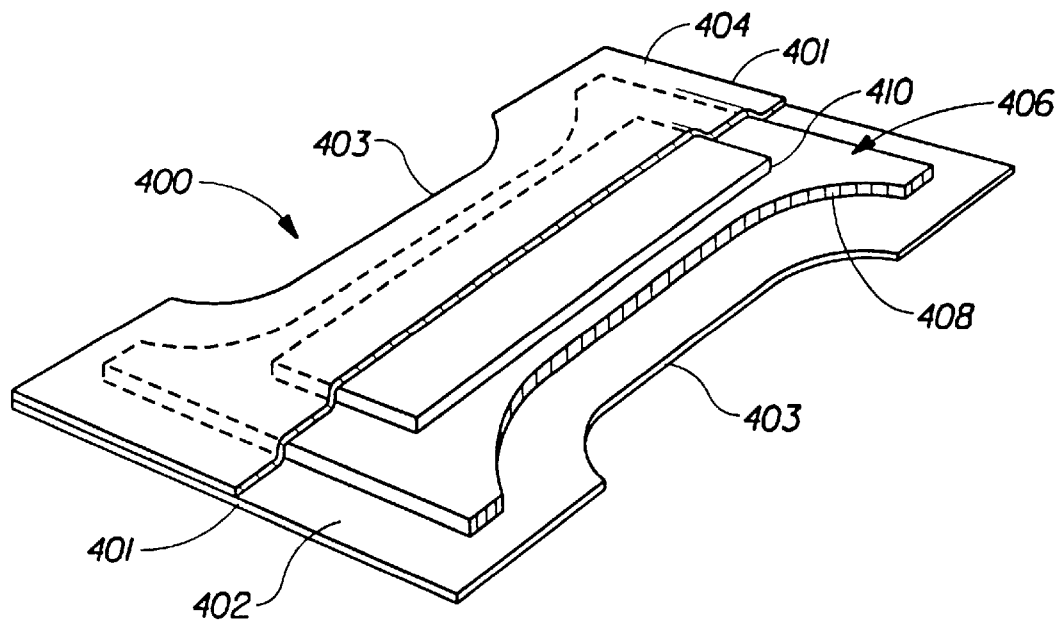
FIG. 18 is an enlarged, partially segmented, perspective illustration of a representative absorbent article in the form of a diaper made in accordance with the present invention.

A representative embodiment of a disposable absorbent article in the form of a diaper 400, is shown in FIG. 18. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like. The diaper 400 depicted in FIG. 18 is a simplified absorbent article that could represent a diaper prior to its being placed on a wearer. It should be understood, however, that the present invention is not limited to the particular type or configuration of diaper shown in FIG. 18.

FIG. 18 is a perspective view of the diaper 400 in its uncontracted state (i.e., with all the elastic induced contraction removed) with portions of the structure being cut-away to more clearly show the construction of the diaper 400. The portion of the diaper 400 which contacts the wearer faces the viewer. The diaper 400 is shown in FIG. 18 to preferably comprise a liquid pervious topsheet 404; a liquid impervious backsheet 402 joined with the topsheet 404; and an absorbent core 406 positioned between the topsheet 404 and the backsheet 402. Additional structural features such as elastic members and fastening means for securing the diaper in place upon a wearer (such as tape tab fasteners) may also be included.

While the topsheet 404, the backsheet 402, and the absorbent core 406 can be assembled in a variety of well known configurations, a preferred diaper configuration is described generally in U.S. Pat. No. 3,860,003 (Buell), issued Jan. 14, 1975, the disclosure of which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; and U.S. Pat. No. 4,816,025 (Foreman), issued Mar. 28, 1989, the disclosures of each of these patents hereby being incorporated herein by reference.

FIG. 18 shows a preferred embodiment of the diaper 400 in which the topsheet 404 and the backsheet 402 are co-extensive and have length and width dimensions generally larger than those of the absorbent core 406. The topsheet 404 is joined with and superimposed on the backsheet 402 thereby forming the periphery of the diaper 400. The periphery defines the outer perimeter or the edges of the diaper 400. The periphery comprises the end edges 401 and the longitudinal edges 403.

The topsheet 404 is compliant, soft feeling, and non-irritating to the wearer's skin. Further, the topsheet 404 is liquid pervious permitting liquids to readily penetrate through its thickness. A suitable topsheet 404 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 404 is made in accordance with the present invention and includes surface energy gradients therein.

A particularly preferred topsheet 404 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 404. For example, the topsheet 404 can be woven, nonwoven, spunbonded, carded, or the like. A preferred topsheet is carded, and thermally bonded by means well known to those skilled in the fabrics art. Preferably, the topsheet 404 has a weight from about 18 to about 25 grams per square meter, a minimum dry tensile strength of at least about 400 grams per centimeter in the machine direction, and a wet tensile strength of at least about 55 grams per centimeter in the crosmachine direction.

The backsheet 402 is impervious to liquids and is preferably manufactured from a thin plastic film, although other flexible liquid impervious materials may also be used. The backsheet 402 prevents the exudates absorbed and contained in the absorbent core 406 from wetting articles which contact the diaper 400 such as bed sheets and undergarments. Preferably, the backsheet 402 is polyethylene film having a thickness from about 0.012 mm (0.5 mil) to about 0.051 centimeters (2.0 mils), although other flexible, liquid impervious materials can be used. As used herein, the term "flexible" refers to materials which are compliant and which will readily conform to the general shape and contours of the wearers body.

A suitable polyethylene film is manufactured by Monsanto Chemical Corporation and marketed in the trade as Film No. 8020. The backsheet 402 is preferably embossed and/or matte finished to provide a more clothlike appearance. Further, the backsheet 402 may permit vapors to escape from the absorbent core 406 while still preventing exudates from passing through the backsheet 402.

The size of the backsheet 402 is dictated by the size of the absorbent core 406 and the exact diaper design selected. In a preferred embodiment, the backsheet 402 has a modified hourglass shape extending beyond the absorbent core 406 a minimum distance of at least about 1.3 centimeters to about 2.5 centimeters (about 0.5 to about 1.0 inch) around the entire diaper periphery.

The topsheet 404 and the backsheet 402 are joined together in any suitable manner. As used herein, the term "joined" encompasses configurations whereby the topsheet 404 is directly joined to the backsheet 402 by affixing the topsheet 404 directly to the backsheet 402, and configurations whereby the topsheet 404 is indirectly joined to the backsheet 402 by affixing the topsheet 404 to intermediate members which in turn are affixed to the backsheet 402. In a preferred embodiment, the topsheet 404 and the backsheet 402 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 404 to the backsheet 402.

Tape tab fasteners (not shown for clarity) are typically applied to the back waistband region of the diaper 402 to provide a fastening means for holding the diaper on the wearer. The tape tab fasteners can be any of those well known in the art, such as the fastening tape disclosed in U.S. Pat. No. 3,848,594 (Buell), issued Nov. 19, 1974, the disclosure of which is hereby incorporated by reference. These tape tab fasteners or other diaper fastening means are typically applied near the corners of the diaper 400.

Elastic members (also not shown for clarity) are disposed adjacent the periphery of the diaper 400, preferably along each longitudinal edge 403, so that the elastic members tend to draw and hold the diaper 400 against the legs of the wearer. Alternatively, the elastic members can be disposed adjacent either or both of the end edges 401 of the diaper 400 to provide a waistband as well as or rather than leg cuffs. For example, a suitable waistband is disclosed in U.S. Pat. No. 4,515,595 (Kievit et al), issued May 7, 1985, the disclosure of which is hereby incorporated by reference. In addition, a method and apparatus suitable for manufacturing a disposable diaper having elastically contractible elastic members is described in U.S. Pat. No. 4,081,301 (Buell), issued Mar. 28, 1978, the disclosure of which is hereby incorporated herein by reference.

The elastic members are secured to the diaper 400 in an elastically contractible condition so that in a normally unrestrained configuration, the elastic members effectively contract or gather the diaper 400. The elastic members can be secured in an elastically contractible condition in at least two ways. For example, the elastic members can be stretched and secured while the diaper 400 is in an uncontracted condition. Alternatively, the diaper 400 can be contracted, for example, by pleating, and the elastic members secured and connected to the diaper 400 while the elastic members are in their unrelaxed or unstretched condition. The elastic members may extend along a portion of the length of the diaper 400. Alternatively, the elastic members can extend the entire length of the diaper 400, or any other length suitable to provide an elastically contractible line. The length of the elastic members is dictated by the diaper design.

The elastic members can be in a multitude of configurations. For example, the width of the elastic members can be varied from about 0.25 millimeters (0.01 inches) to about 25 millimeters (1.0 inch) or more; the elastic members can comprise a single strand of elastic material or can comprise several parallel or non-parallel strands of elastic material; or the elastic members can be rectangular or curvilinear. Still further, the elastic members can be affixed to the diaper in any of several ways which are known in the art. For example, the elastic members can be ultrasonically bonded, heat and pressure sealed into the diaper 400 using a variety of bonding patterns or the elastic members can simply be glued to the diaper 400.

The absorbent core 406 of the diaper 400 is positioned between the topsheet 404 and the backsheet 402. The absorbent core 406 can be manufactured in a wide variety of sizes and shapes (e.g., rectangular, hourglass, asymmetrical, etc.). The total absorbent capacity of the absorbent core 406 should, however, be compatible with the design liquid loading for the intended use of the absorbent article or diaper. Further, the size and absorbent capacity of the absorbent core 406 can vary to accommodate wearers ranging from infants through adults.

As shown in FIG. 18, the absorbent core 406 includes a fluid distribution member 408. In a preferred configuration such as depicted in FIG. 18, the absorbent core 406 preferably further includes an acquisition layer or member 410 in fluid communication with the fluid distribution member 408 and located between the fluid distribution member 408 and the topsheet 404. The acquisition layer or member 410 may be comprised of several different materials including nonwoven or woven webs of synthetic fibers including polyester, polypropylene, or polyethylene, natural fibers including cotton or cellulose, blends of such fibers, or any equivalent materials or combinations of materials.

In use, the diaper 400 is applied to a wearer by positioning the back waistband region under the wearer's back, and drawing the reminder of the diaper 400 between the wearer's legs so that the front waistband region is positioned across the front of the wearer. The tape-tab or other fasteners are then secured preferably to outwardly facing areas of the diaper 400.

PREPARATION OF REPRESENTATIVE ABSORBENT ARTICLES

The following is a description of a suitable method for constructing a representative absorbent article including a fluid transport web according to the present invention.
Preparation of Treated Topsheets SYL-OFF 7048 Crosslinker is mixed at a 10% added on level to SYL-OFF 7677 Release Coating, both from Dow Corning. This silicone mixture is then liberally applied to a sheet of paper towel commercially available from The Procter & Gamble Company of Cincinnati Ohio, under the trade name Bounty®. The particular towel variety utilized does not have a distinctly-visible surface pattern embossed therein. After the mixture has soaked into the paper towel the excess SYL-OFF mixture is removed by blotting with a dry towel so as to avoid visible pooling of free silicone material. This paper towel hereafter is referred to for convenience as the "treated towel".

Topsheets are cut to the desired dimension from a sheet of topsheet material and taped to paper towels (Bounty®) as a carrier material so that the garment-facing side of the topsheet is facing the carrier material. The wearer-contacting side of the taped topsheet is then placed onto the treated towel. A roller (of the type commercially available from art supply stores which is known as a printing block roller, such as the "Speedball" roller from Hunt Mfg. Co.) is then gently passed over the back of the taped topsheet paper towel so that the wearer-contacting surface of the topsheet contacts the treated towel. The taped topsheet is then immediately hung wearer-contacting-side-down in a 60° C. non-air-circulating oven and allowed to cure for 10 minutes. To insure complete curing has occurred, the tape on the topsheet may be inspected to be sure that the SYL-OFF mure does not rub off.

After curing, the tape and paper towel are removed from the topsheet and the topsheet is cut to a desired size and shape (still larger than the finished absorbent article) from the central (non-taped) portion of the topsheet material. This is done to remove the taped area from the topsheet before the topsheet is weighed to calculate the basis weight of the SYL-OFF on the topsheet.

The basis weight of the SYL-OFF material is determined by subtracting the basis weight of the topsheet material in an uncoated condition (grams per square meter) from the basis weight (grams per square meter) of the coated topsheet material. If the basis weight of the uncoated starting topsheet material is not known beforehand, the starting topsheet may be cut to a known size and weighed before initiating the coating procedure.

In order to obtain various coating weights of silicone on the topsheet material, a number of parameters may be varied as required. Such parameters include the roller pressure during its application to the topsheet material, the number of passes of the roller over the topsheet material, the viscosity of the silicone material (which may be influenced by temperature, for example), the saturation level of the treated towel, etc.

Topsheets formed from an initially-hydrophilic material are then ready to be applied to a catamenial pad. Topsheets formed from an initially-hydrophobic material are treated with a solution of 0.1% Pegosperse 200ML to render the non-silicone-coated areas hydrophilic. The garment-facing surface of such topsheets is dipped into a suitable-sized pan of the Pegosperse 200ML solution. The topsheet is then immediately hung wearer-contacting side up in a 60° C. oven non-air circulating oven until dry. The topsheet is then ready to be placed onto a catamenial pad.

Preparation of Catamenial Pads

Catamenial pads are constructed as follows. Onto silicone-coated release paper a spiral pattern of H2031 Findlay hot melt adhesive is applied at 0.04 g per in$^2$. This adhesive layer is transferred onto the top (wearer-facing) side of a secondary topsheet by rolling the secondary topsheet and coated release paper together with a hand roller. The secondary topsheet is formed of a nonwoven material known as Fort Howard Airlaid Tissue, Grade 817, commercially available from the Fort Howard Corp. of Green Bay, Wis. The topsheet is applied to the adhesive side of the secondary topsheet and the two are bonded by gently pressing them together with a hand roller. Two strips of one-quarter-inch double-sided tape are applied on along both long sides of a polyethylene backsheet. The absorbent core is added to construct the complete absorbent structure.

Figure 19:
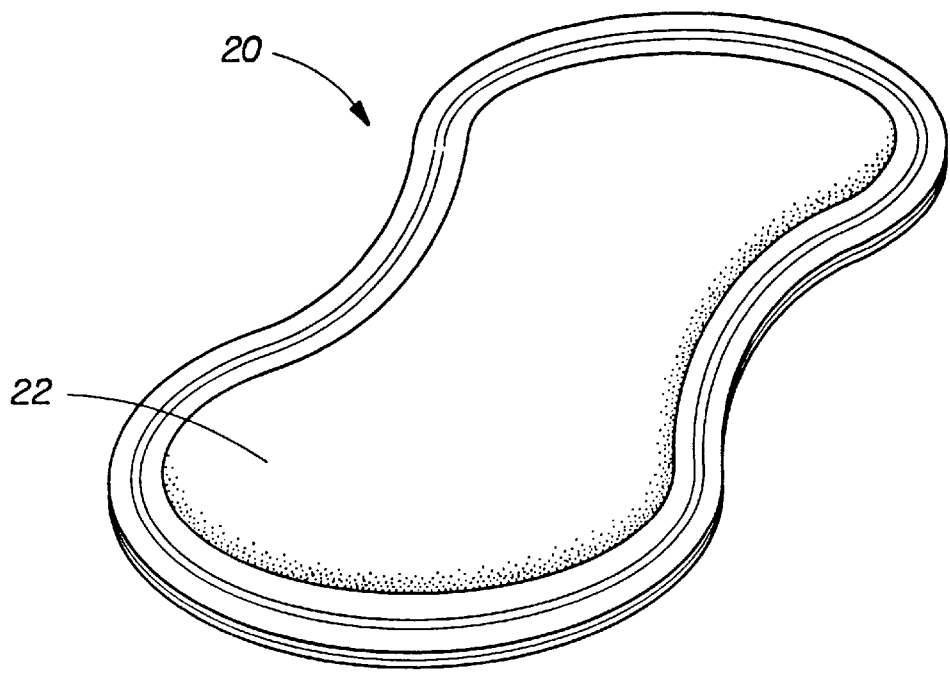
FIG. 19 is an enlarged, perspective illustration of a representative absorbent article in the form of a sanitary napkin or catamenial pad made in accordance with the present invention.

To construct a representative absorbent article according to the embodiment of FIG. 19, the following materials are utilized for the components of the absorbent structure. The absorbent article of FIG. 19 (catamenial pad) is structurally similar to that of FIGS. 14–17, except that it exhibits an hourglass-shaped overall profile. The core layer is assembled as follows: A sheet of the same Fort Howard material as the secondary topsheet is cut to a finished size of 190 mm by 143 mm. A silicone-coated release paper containing a spiral pattern of H2031 Findlay hot melt adhesive is applied to the Fort Howard at 0.04 grams per square inch. The silicone-coated release paper which is used to transfer the glue is left on the Fort Howard and a 190 mm by 65 mm template is placed onto the middle of the sheet with the lengthwise ends aligned with the lengthwise ends of the Fort Howard. The Fort Howard is then folded over the template to crease the material, dividing the material into three portions. The template is then removed, leaving the glue on the creased Fort Howard. Particulate absorbent gelling material in the form of Nalco 1180 AGM is then evenly distributed in the amount of 0.68 grams per pad onto the glue side of the Fort Howard, nonwoven material. Next, 190 mm of quarter inch double-sided tape is then applied to the inside edge of the Fort Howard, which is then folded over by the creases so that the taped edge is on top. The resulting storage core has a finished dimension of 190 mm by 65 mm. The secondary topsheet is adhesively bonded to the topsheet. The storage/core layer is adhesively bonded to the polyethylene backsheet by two strips of quarter inch double-sided tape.

The topsheet and absorbent structure assembly are then combined. Next, a sheet of Teflon® is placed over the assembled structure. The edges of the product are sealed with an appropriately shaped die, attached to an iron and heated to a temperature above the melting point of the polyethylene topsheet and backsheet. The iron die is applied to the material with hand pressure to seal the edges. The catamenial pad is then cut from the excess material using a pair of hand scissors.

EXAMPLES

Example 1

A topsheet was prepared according to the procedure set forth above. The starting material was a three-dimensional, macroscopically-expanded, formed film generally in accordance with the 1342 Radel et al. and '045 Ahr et al. patents described above, which is marketed on sanitary napkins by The Procter & Gamble Company of Cincinnati, Ohio as "DRI-WEAVE". The film had the general appearance of the film depicted in FIG. 1 above, and contained a resin-incorporated surfactant (RIS) so as to be generally hydrophilic in nature. The topsheet was coated with silicone on the wearer-contacting surface at a rate of 0.47 grams per square meter and, in accordance with the procedure above, was incorporated into an absorbent article in the form of a catamenial pad having the overall appearance of the catamenial pad depicted in FIG. 19.

Example 2

A topsheet was prepared according to Example 1, with the exception of the coating weight of silicone which was 1.3 grams per square meter, and was incorporated into an absorbent article in the form of a catamenial pad having the overall appearance of the catamenial pad depicted in FIG. 19.

Example 3

A topsheet was prepared according to the procedure set forth above. The starting material was a non-apertured nonwoven web of polypropylene fibers commercially available as Diaper Topsheet P8 (23 grams per square meter) from Veratec of Walpole, Mass., which was generally hydrophilic in nature. The topsheet was coated with silicone on the wearer-contacting surface at a rate of 0.50 grams per square meter and, in accordance with the procedure above, was incorporated into an absorbent article in the form of a catamenal pad having the overall appearance of the catamenial pad depicted in FIG. 19.

Example 4

A topsheet was prepared according to Example 3, with the exception of the coating weight of silicone which was 2.7 grams per square meter, and was incorporated into an absorbent article in the form of a catamenial pad having the overall appearance of the catamenial pad depicted in FIG. 19.

Example 5

A topsheet was prepared according to the procedure set forth above. The starting material was a three-dimensional, macroscopically-expanded, formed film having microapertures in accordance with the '643 Curro patent described above. The film was similar in overall impression to the film depicted in FIG. 10 above. The topsheet was coated with silicone on the wearer-contacting surface at a rate of 0.52 grams per square meter, topically treated with surfactant in the manner described above and, in accordance with the procedure above, was incorporated into an absorbent article in the form of a catamenial pad having the overall appearance of the catamenial pad depicted in FIG. 19.

Example 6

A topsheet was prepared according to Example 5, with the exception that the coating weight of silicone was 1.08 grams per square meter, and was incorporated into an absorbent article in the form of a catamenial pad having the overall appearance of the catamenial pad depicted in FIG. 19.

ANALYTICAL METHODS

The following are representative anyical methods which have been found suitable for and useful in determining the performance of fluid transport webs in accordance with the present invention. The analytical methods described herein are preferably accomplished utilizing a particular standard fluid referred to as artificial menstrual fluid (hereafter referred to as "AMF"), although similar analytical studies could be undertaken with other fluids. Formulation and preparation of a suitable artificial menstrual fluid are described in the Test Methods section of allowed, commonly-assigned, co-pending U.S. Pat. No. 5,604,414 issued on Mar. 4, 1997 to Richards et al., the disclosure of which is hereby incorporated herein by reference.

1. Acquisition Rate.

Acquisition rate, as utilized herein, is a measure of the time required for a given volume of surface-applied liquid to enter, or "strikethrough", a topsheet material into an underlying absorbent structure. In the present series of tests it is a measure of the time in seconds to completely drain 7.5 milliliters of AMF solution having a surface tension of 46–58 dynes/cm from a one inch diameter by ⅝ inch deep cavity having a multiplicity of holes in its lowermost surface. Other suitable fluid volumes include 17 milliliters and 5 milliliters. The cavity is integrally formed in a 4 inch×4 inch strikethrough plate which is placed on a complete absorbent article fabricated in accordance with the description above including the topsheet to be tested. The wearer-contacting surface of the topsheet sample is oriented face-up. An electric timer is started by the AMF solution contacting a pair of spaced electrodes in the aforedescribed cavity. The timer automatically shuts off when all of the AMF solution has drained from the cavity and into the absorbent element. Times are reported in seconds.

2. Dryness.

Dryness, as utilized herein is a measure of how readily fluid can migrate upward onto the wearer-contacting surface of the topsheet after fluid acquisition, as well as residual wetness on the topsheet surface. Accordingly, 90 seconds after the completion of the AMF acquisition in the above acquisition rate test, the strikethrough plate is removed and a preweighed sample of filter paper approximately 5 inches×5 inches is inserted over the uppermost surface of the topsheet of the absorbent article sample, and a predetermined pressure loading of 0.25 psi. is applied to the sample for a period of 30 seconds. The filter paper is then removed and reweighed, and the amount of fluid absorbed by the filter paper is termed the "surface wetness" of the sample. Results are expressed in grams of fluid absorbed by the filter paper. Other suitable time increments include 20 minutes after completion of the AMF acquisition. As should thus be apparent, a lower "surface wetness" number is indicative of a dryer surface feel. More conveniently, "dryness" may be expressed as 1/surface wetness, which results in larger dryness values equating to dryer surface feel.

3. Masking.

As utilized herein, the term "masking" is defined as the difference in intensity of reflected light between a "used" or soiled product and its initial intensity reading before use. The acceptance of a catamenial product strongly depends on the masking performance of its topsheet. In fact, good masking not only provides a cleaner and drier topsheet surface but also reflects better absorbency and less rewet of the product. Masking may be analyzed by measuring the intensity of light reflected from the product's surface after it has been wetted, in order to be able to quantify it and compare results among different products.

The intensity of the light describes the energy of the light. The incoming (incident) light beam (e.g., sun light) is reflected by the surface and creates an outgoing (reflected) light beam that has a different energy or intensity. The difference of the intensities of the incoming and outgoing beam is the energy that the surface absorbs. For instance, a black surface absorbs significantly more energy or light than a white surface. The energy that is absorbed by the black surface may be transformed in heat. Therefore, black cars tend to be wanner than white cars in the summer. The intensity of the light strongly depends on the light source. Typically the intensity of the light may be characterized using different gray levels. Hence, white would acquire a value equal zero (white=0) and black the value 255 (black=255). Any gray (or intensity of the light) between these two values will be anywhere 0 and 255.

A sample product for evaluation is analyzed before introduction of any fluid, i.e., in its unused condition. A measurement area is defined and a set of measurements is taken. Results from 5 measurements are averaged. The samples are then infused with 5 ml of fluid in accordance with the procedure enunciated with regard to the acquisition test to perform the wet measurement. Before removing the strikethrough plate and subjecting the sample to the masking measurement and analysis, 3 minutes is allowed to elapse for the fluid to reach a steady state orientation within the sample. A second set measurements is then taken of the same product using the same identified measurement area. Results from 5 measurements are averaged. The numerical difference between the average initial reading and the average after-use reading provides a quantification of the difference in reflected light, and hence the cleanliness of the surface of the product. Low numerical differences reflect little change from pre-use condition, and hence effective "masking", while higher differences reflect a greater change from pre-use condition and hence less effective "masking".

The following is a description of suitable components and a suitable method for assessing masking performance of a fluid transport web according to the present invention.

Hardware Components

The scanner utilized is a conventional HP Scanner IIp connected to an Apple Macintosh computer. The computer should have at least 8 MB RAM memory in order to be able to run the scanner software and NIH Image at the same time. The monitor should have at least 256 gray levels to run the software.

Software Components

Scanner Software (DeskScan II 2.1)

This software is provided by HP and designed to run with the HP Scanner IIp.

NIH Image Version 1.44

This program allows individuals to analyze a picture and determine the density of any color or gray level and the intensity of reflected light.

Measuring Procedures

The following describe in detail the procedure for measuring a catamenial pad or a siilar object.

Data Determination

The flatness of the sample's surface is very important, in order to get consistent results. At this point, a 12" metal ruler weighing 42.8 grams is placed on the length of the catamenial to flatten the sample sufficiently to perform the measurements without unduly compressing or distorting the sample.

After scanning wet samples the screen is cleaned with an alcohol-impregnated soft tissue. The scanner screen must always be very dean, since dirt on the screen may affect the quality of a scanned sample and the measurement.

Using the Scanner

Following steps are necessary to scan a sample with the HP IIp scanner:

Preparing the Scanner:
1. Make sure the scanner is plugged into the computer
2. Start the computer
3. Switch on the scanner
4. Start the Scanner software program (DeskScan II 2.1)

Scanning an Image:
5. Place the pad on the center of the screen
6. Place the weight (e.g., a metal ruler) on the pad.
7. Press PREVIEW on the menu of the program
8. Select the type of image you want to have. (Choose: Black and white photo!!)
9. Select the print path (Choose: Lintronic)
10. Select the area you want to save into a file.
11. Adjust the brightness and contrast
    Brightness: 114
    Contrast: 115
These values must be set, in order to have always the same quality of the image
12. Make sure that you have all the correct settings
13. Push the FINAL button
    The system will ask you to define a name and a folder to store the file. The file should have a TIFF format. Usually this option is preset. But make sure you save the file in TIFF format, in order to be able to open this file in NIH Image.
    The scanner will then scan your pad again, this time slower, because it saves the picture in a file.

Data Evaluation

The following steps describe the procedure of anaig a scanned picture.

Analyzine the Scanned Picture Using NIH Image

Customizing the Program
1. Open NIH Image.
2. Customize the program (only when you first use it!)
    a) Menu: OPTIONS
       Check Gray scale
       Preferences:—Undo & Clipboard buffer: set to 1500 K
          Record preferences in FILE menu
    b) Menu: ANALYZE
       Options:—Check Area and Mean Density
          Digits right of . . . : set to 1
    c) Restart NIH Image to make all the settings effective
Measuring
3. Open the calibration file named CALIBRATION.TIFF
4. Open the scanned file in TIFF format
    If the system warns you that the Undo Buffer is too small, add memory repeating preferences in step 2a).
    The measurements for the scanned file will be automatically calibrated, as long as the CALIBRATION.TIFF file is open at the same time. You can check if the picture has been calibrated, if there is a white diamond displayed in the title bar.
5. Go to ANALYZE in the menu and select RESET
6. Start measuring
    a) Select an area to be measured (you may choose a square box of about 0.4×0.4 in.) which is smaller than the area subjected to the fluid staining.
    b) Go to ANALYZE in the menu and select MEASURE
    c) Repeat steps 6a) and b) for a total of 5 measurements of different sample "square boxes" within the region of interest.
    d) Go to ANALYZE in the menu and select SHOW RESULTS
7. Close the file without saving
8. Repeat steps 4–7 until you finished the measurements While particular embodiments of the present invention have been illustrated and described, it would be obvious to those skilled in the art that various other changes and modifications can be made without departing from the spirit and scope of the invention It is therefore intended to cover in the appended claims all such changes and modifications that are within the scope of this invention.

What is claimed is:

1. A web having first and second surfaces, said web comprising:
    (a) a plurality of fluid passageways placing said first and second surfaces in fluid communication with one another; and
    (b) a plurality of microscopic, spaced regions disposed on said first surface, said regions having a first surface energy which is lower than a second surface energy of the remainder of said web, a difference between said first and second surface energies defines a surface energy gradient which is adapted to exert a force on fluid contacting said first surface, such that said fluid will be directed toward said fluid passageways for transportation away from said first surface and in the direction of said second surface.

2. The web of claim 1, wherein said first surface includes land areas between adjacent fluid passageways, said regions being located on said land areas.

3. The web of claim 1, wherein said regions are also located at least partially within said fluid passageways.

4. The web of claim 1, wherein said fluid passageways comprise capillaries, and wherein said regions are located at least partially within said capillaries.

5. The web of claim 1, wherein said fluid passageways comprise capillaries, and wherein said first surface includes land areas between adjacent capillaries.

6. The web of claim 1, wherein at least one fluid passageway exhibits a plurality of said regions located at least partially within said fluid passageway.

7. The web of claim 1, wherein said regions are randomly distributed over said first surface.

8. The web of claim 1, wherein said regions are randomly located at least partially within said fluid passageways.

9. The web of claim 8, wherein said regions are randomly located between said first and second surfaces.

10. The web of claim 3, wherein said regions are located within said fluid passageways at random distances from said first surface.

11. The web of claim 3, wherein at least one fluid passageway exhibits a plurality of said regions located at different distances from said first surface.

12. The web of claim 1, wherein said regions are located at least partially on said first surface and extend at least partially into said fluid passageways.

13. The web of claim 1, wherein said regions exhibit a work of adhesion for water of less than about 75 erg/cm$^2$.

14. The web of claim 1, wherein said web comprises a nonwoven material.

15. The web of claim 1, wherein said web comprises a polymeric film material.

16. The web of claim 1, wherein said web comprises an apertured, macroscopically-expanded formed film.

17. The web of claim 1, wherein said web comprises a composite material having a nonwoven component and a polymeric film component.

18. The web of claim 1, wherein said web includes microapertures.

19. The web of claim 18, wherein said regions are also located within said microapertures.

20. The web of claim 1, wherein said web includes microscopic surface aberrations.

21. An apertured, three-dimensional, macroscopically-expanded, formed film web having first and second surfaces, said web comprising:
   (a) a plurality of apertures placing said first and second surfaces in direct fluid communication with one another; and
   (b) wherein said first surface consists essentially of a first material which exhibits a first surface energy and said second surface consists essentially of a second material which exhibits a second surface energy which is greater than said first surface energy, and said second material extends, at least partially into said apertures.

22. The web of claim 1, wherein said web comprises a hydrophilic flexible network of interconnected open spaces forming fluid passageways in a polymeric foam material.

23. The web of claim 1, wherein said difference in surface energy comprises a difference in work of adhesion for water of at least about 50 erg/cm$^2$.

24. The web of claim 1, wherein said web comprises a topsheet on an absorbent article.

25. The web of claim 24, wherein said absorbent article comprises a catamenial pad.

26. The web of claim 24, wherein said absorbent article comprises a diaper.

27. The web of claim 1, wherein said web comprises an absorbent structure in an absorbent article.

28. The web of claim 1, wherein said web comprises a towel product.

29. The web of claim 1, wherein said material comprises a curable silicone material.

30. The web of claim 1, wherein said material comprises a fluoropolymer.

31. An absorbent article comprising:
   (a) a topsheet, said topsheet comprising a web according to claim 1;
   (b) a backsheet; and
   (c) an absorbent structure located between said topsheet and said backsheet.

\* \* \* \* \*